United States Patent
Lee et al.

(10) Patent No.: US 11,873,326 B2
(45) Date of Patent: Jan. 16, 2024

(54) CELL LINE WHICH IS KNOCK OUT THE BMP RECEPTOR GENES AND A METHOD OF PRODUCING TARGET PROTEINS USING THE SAME

(71) Applicant: KOREA ADVANCED INSTITUTE OF SCIENCE AND TECHNOLOGY, Daejeon (KR)

(72) Inventors: Gyun-Min Lee, Daejeon (KR); Che Lin Kim, Daejeon (KR)

(73) Assignee: Korea Advanced Institute of Science and Technology

( * ) Notice: Subject to any disclaimer, the term of this patent is extended or adjusted under 35 U.S.C. 154(b) by 1001 days.

(21) Appl. No.: 16/556,725

(22) Filed: Aug. 30, 2019

(65) Prior Publication Data
US 2020/0262883 A1 Aug. 20, 2020

(30) Foreign Application Priority Data
Feb. 15, 2019 (KR) .................. 10-2019-0018104

(51) Int. Cl.
*C07K 14/51* (2006.01)
*C12N 15/10* (2006.01)
*C12N 15/113* (2010.01)

(52) U.S. Cl.
CPC ............ *C07K 14/51* (2013.01); *C12N 15/102* (2013.01); *C12N 15/1136* (2013.01); *C12N 2810/40* (2013.01)

(58) Field of Classification Search
CPC ... C12N 15/1136; C12N 15/102; C07K 14/51
See application file for complete search history.

(56) References Cited

PUBLICATIONS

Cha et al. J. Microbiol. Biotechnol, 2017; 27(7), 1281-1287. (Year: 2017).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Bork Genome Research, 2000, 10:398-400 (Year: 2000).*
Cha et al. "Expression and Purification of Biologically Active Human Bone Morphogenetic Protein-4 in Recombinant Chinese Hamster Ovary Cells," Journal of Microbiology and Biotechnology, 2017, vol. 27, No. 7, pp. 1281-1287.
Gautschi et al. "Bone Morphogenetic Proteins in Clinical Applications," ANZ Journal of Surgery, 2007, vol. 77, pp. 626-631.
Rahman et al. "TGF-β/BMP signaling and other molecular events: regulation of osteoblastogenesis and bone formation," Bone Research, 2015, vol. 3, 15005, 20 pages.

* cited by examiner

*Primary Examiner* — Vanessa L. Ford
*Assistant Examiner* — Sandra Dillahunt
(74) *Attorney, Agent, or Firm* — Sheridan Ross P.C.

(57) ABSTRACT

The present invention relates to a transgenic CHO cell line in which the BMP receptor gene BMPRIA or BMPRII is knocked out. The BMP type I receptor BMPRIA or BMP type II receptor BMPRII gene which plays an important role in intracellular signal transduction in CHO cells is knocked out to prevent the activation of self concentration control pathway and the signal transduction mediated by BMP in CHO cells, so that the productivity of a target protein to be produced can be improved.

16 Claims, 7 Drawing Sheets
Specification includes a Sequence Listing.

Figure 2

*BMPR1A* KO clone #22

```
5' AGTAACACTTTAAGAAAGGCAAAGTATCCT-CCGGGGCTAAAGTCACTCCATT3'   Wild type
   AGTAACACTTTAAGAAAGGC----------------TAAAGTCACTCCATT       Δ17
   AGTAACACTTTAAGAAAGGCAAAGT----T-CCGGGGCTAAAGTCACTCCATT     Δ4
   AGTAACACTTTAAGAAAGGCAAAGTATCCTTCCGGGGCTAAAGTCACTCCATT     +1
```

*BMPR1A* KO clone #35

```
5' AGTAACACTTTAAGAAAGGCAAAGTATCCT--CCGGGGCTAAAGTCACTCCATT3'  Wild type
   AGTAACACTTTAAGAAAGGCAAAGTAT--T--CCGGGGCTAAAGTCACTCCATT    Δ2
   AGTAACACTTTAAGAAAGGCAAAGTA------CCGGGGCTAAAGTCACTCCATT    Δ4
   AGTAACACTTTAAGAAAGGCAAAGTATCCTT-CCGGGGCTAAAGTCACTCCATT    +1
   AGTAACACTTTAAGAAAGGCAAAGTATCCTTTCCGGGGCTAAAGTCACTCCATT    +2
```

*BMPR1A* KO clone #43

```
5' AGTAACACTTTAAGAAAGGCAAAGTATCCT-CCGGGGCTAAAGTCACTCCATT3'   Wild type
   AGTAACACTTTAAGAAAGGCAAAGTATCCTTCCGGGGCTAAAGTCACTCCATT     +1
```

*BMPR1A* KO clone #47

```
5' AGTAACACTTTAAGAAAGGCAAAGTAT-CCTCCGGGGCTAAAGTCACTCCATT3'   Wild type
   AGTAA----------------------------AGTCACTCCATT             Δ35
   AGTAACACTTTAAGAAAGGCAAAGTATA---CCGGGGCTAAAGTCACTCCATT     Δ3, +1
```

*BMPR1A* KO clone #61

```
5' AGTAACACTTTAAGAAAGGCAAAGTATCCTC----------------------------------CGGGGCTAAAGTCACTCCATT3'  Wild type
   AGTAACACTTTAAGAAAGGCAAAGTATCCTCAGACCATCCTGGACTTCCTGAAGAGCGACGGCTTCGCC-
                            --AACCGCAACTTCATGCAGCTGATCCACGACGACAGCCTG-
                                  -ACCTTCAAGGAGGACATCCAGAAGGCCCAGGTGAGCGTCGGGGCTAAAGTCACTCCATT   +115
```

*BMPR1A* KO clone #68

```
5'AGTAACACTTTAAGAAAGGCAAAGTATCCTC---------------------------------------CGGGGCTAAAGTCACTCCATT3'  Wild type
  AGTAACACTTTAAGAAAGGCAAAGTATCCTCTGGTCTTGGAACACTTCCAAATCTCAGTGAAAAGCGAAGCCAGTGTTTCCGGGGCTAAAGTCACTCCATT   +49
```

CELL LINE WHICH IS KNOCK OUT THE BMP RECEPTOR GENES AND A METHOD OF PRODUCING TARGET PROTEINS USING THE SAME

CROSS-REFERENCE TO RELATED APPLICATIONS

This application claims the benefit of the Republic of Korea Patent Application No. KR10-2019-0018104 filed Feb. 15, 2019, the entire contents of which are incorporated herein by reference.

REFERENCE TO A SEQUENCE LISTING

This application contains a Sequence Listing submitted electronically as a text file by EFS-Web. The text file, named "Sequence_List_ST25_sub", has a size in bytes of 42000 bytes, and was recorded on Sep. 12, 2019. The information contained in the text file is incorporated herein by reference in its entirety pursuant to 37 CFR § 1.52(e)(5).

BACKGROUND OF THE INVENTION

1. Field of the Invention

The present invention relates to a transgenic CHO cell line in which the BMP receptor gene is knocked out.

2. Description of the Related Art

Bone morphogenetic protein (BMP) is a growth factor belonging to transforming growth factor β (TGF-β) superfamily. There are 14 kinds of BMPs, from BMP-2 to BMP-15, which are known to play an important role in osteoblast differentiation and subsequent bone formation (TGF-β signaling and other molecular events: regulation of osteoblastogenesis and bone formation Rahman et al., Bone Res. 2015 Apr. 14; 3:15005). Recombinant BMPs, particularly BMP-2, BMP-4 and BMP-7, have been reported to have the ability to treat bone injuries in rodents, dogs, sheep, and primates (BONE MORPHOGENETIC PROTEINS IN CLINICAL APPLICATIONS. Gautschi et al., ANZ J Surg. 2007 August;77(8):626-31). Many studies related to therapeutic recombinant BMPs have been actively going on, and the products using BMP2 or BMP7 have been commercialized and used for medical purposes.

For the mass-production of therapeutic recombinant proteins including BMP, CHO dhfr(−) cell line, CHO K1 cell line, BHK cell line and NSO cell line have been industrially used. Among those cell lines, dihydrofolate reductase (DHFR) deficient CHO cell line is the cell line that is most widely used for the industrial mass-production of a therapeutic recombinant protein. The reasons why the DHFR deficient CHO cell line is most preferred industrially are as follows: (1) Posttranslational modification process such as glycosylation and phosphorylation is similar to that of human cells so that immune response of the human body can be minimized, indicating that a therapeutically effective recombinant protein in the human body can be produced. (2) Suspension culture is possible, which favors high concentration culture and mass-production process. (3) High therapeutic recombinant proteins can be produced using dihydrofolate reductase (DHFR)/methotrexate (MTX) gene amplification system. (4) Stability has been proved through long term study so that it is easy to get approval from the supervisory agency such as FDA.

As the demand of a therapeutic recombinant protein using CHO cells is greatly increased, various studies to increase the productivity of a therapeutic recombinant protein have been conducted. In particular, the method to increase the production of a therapeutic recombinant protein per unit cell by adding an additive is one of the most efficient methods.

On the other hand, all members of the TGF-β superfamily including BMP bind to serine-threonine kinase receptor on the cell surface to activate a pathway in a certain cell that activates gene transcription. BMP binds to BMP type II receptor and recruits BMP type I receptor to form a heterodimeric complex. Upon BMP binding, type I receptor kinase activates intracellular signaling pathways including the Smad protein signaling pathway. The phosphorylated Smad1/5/8 complex interacts with Smad 4 and moves into the nucleus to control the transcription of various target genes. It is well known that BMP signals regulate important cellular processes such as cell proliferation and death. In relation to that, it has been reported that cell proliferation was reduced but apoptosis was increased in various types of cells including cancer cells, sympathetic nerve bundle precursor cells and human pulmonary smooth muscle cells after the treatment of BMP-4. Since BMP regulates many cellular functions, the expression and activity of BMP are regulated at the multimolecular level including transcriptional and post-transcriptional regulations. In particular, it was observed that as osteoblasts were exposed on the recombinant human BMP-4 (rhBMP-4) longer, the half-life of BMP-4 gene mRNA became shorter and the transcription rate was reduced, suggesting that the expression of BMP-4 was directly inhibited by BMP. These results suggest that inadequate cell growth and negative autoregulation of BMP-4 gene including post-transcriptional regulation of BMP-4 mRNA would contribute to low rhBMP-4 productivity in CHO cells. Since an essential element for BMP signaling pathway is expressed in CHO DG44 host cells, the CHO cell line expressing rhBMP-4 is affected by rhBMP-4 mediated signaling and have unexpected cellular functions.

To overcome the problems above, the present inventors constructed CHO cell lines in which the BMP receptor genes BMP type I receptor (BMPRIA) and type II receptor (BMPRII) which are necessary for BMP signaling were removed. The present inventors further confirmed that the BMP receptor deficient cell line demonstrated higher recombinant protein productivity, compared with the wild type cell line, leading to the completion of the present invention.

PRIOR ART REFERENCE

Non-Patent Reference (Non-patent Reference 1) Rahman MS et al., Bone Res. 2015 Apr. 14; 3:15005

SUMMARY OF THE INVENTION

It is an object of the present invention to provide a transgenic CHO cell line in which the BMP receptor gene BMPRIA or BMPRII is knocked-out.

It is another object of the present invention to provide a preparation method of a transgenic CHO cell line in which the BMP receptor gene BMPRIA or BMPRII is knocked-out.

It is also an object of the present invention to provide a production method of a target protein using a transgenic CHO cell line in which the BMP receptor gene BMPRIA or BMPRII is knocked-out.

To achieve the above objects, the present invention provides a transgenic CHO cell line in which the BMP receptor gene BMPRIA or BMPRII is knocked-out.

The present invention also provides a preparation method of a transgenic CHO cell line in which the BMP receptor gene BMPRIA or BMPRII is knocked-out, which comprises the following steps:

1) constructing a vector to knock-out the BMP receptor gene BMPRIA or BMPRII;
2) introducing the vector of step 1) into a CHO cell line; and
3) selecting the CHO cell line in which the BMP receptor gene BMPRIA or BMPRII has been knocked-out from those CHO cell lines introduced with the vector of step 2).

In addition, the present invention provides a production method of a target protein, which comprises the following steps:

1) introducing a vector containing the nucleotide sequence encoding a target protein into the transgenic CHO cell line of claim 1 in which the BMP receptor gene BMPRIA or BMPRII has been knocked-out;
2) culturing the cell line prepared in step 1) above; and
3) separating and purifying the target protein produced in step 2) above.

Advantageous Effect

The BMP type I receptor BMPRIA or BMP type II receptor BMPRII gene which plays an important role in intracellular signal transduction in CHO cells is knocked out to prevent the activation of self concentration control pathway and the signal transduction mediated by BMP in CHO cells, so that CHO cell growth increases, leading to the improvement of the productivity of a target protein to be produced.

BRIEF DESCRIPTION OF THE DRAWINGS

FIG. 2 is a diagram illustrating the nucleotide sequences of knock-out target sequences in the BMPRIA gene knock-out clones (22, 35, 43, 47, 61 and 68).

DESCRIPTION OF THE PREFERRED EMBODIMENTS

Figure 1:
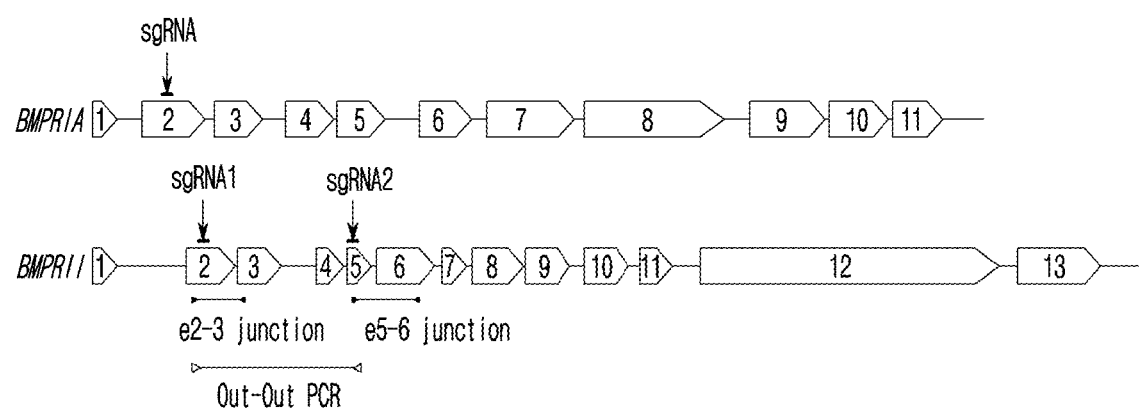
FIG. 1 is a diagram illustrating the structures of BMPRIA gene and BMPRII gene in CHO cells, the location of sgRNA targeting each BMP receptor gene and the primer binding sites of junction PCR and out-out PCR.

Hereinafter, the present invention is described in detail.

The present invention provides a transgenic CHO cell line in which the BMP receptor gene BMPRIA or BMPRII is knocked-out.

The said BMPRIA gene is a BMP type I receptor gene and the said BMPRII gene is a BMP type II receptor gene.

Particularly, the cell line above can have a mutation in the nucleotide sequence of the $2^{nd}$ exon of the BMPRIA gene. More particularly, the cell line can have a mutation in the nucleotide sequence 5'-ATGCATGTGTTATTAATAGCAT-CATCTGGGCAGTGGCCTGAGCAGTAACACTT-TAAGAA AGGCAAAGTATCCTCCGGGGCTAAAGT-CACTCCATTTTCTGGCTTCTTCTGGTCCAAGT CTGATTTCATACCAGTACCATGGAGCATACTGTCTA-GATTCTGCC-3' (SEQ. ID. NO: 1) of the $2^{nd}$ exon of the BMPRIA gene. More precisely, the BMPRIA gene knock out transgenic CHO cell line has been transfected with a vector comprising the nucleotide sequences represented by SEQ. ID. NO: 10 and SEQ. ID. NO: 13, so that the nucleotide sequence of the $2^{nd}$ exon of the BMPRIA gene has been mutated.

In addition, the cell line can have a mutation in the nucleotide sequences of the $2^{nd}$ to $5^{th}$ exons of the BMPRII gene. More particularly the cell line can have a mutation in the nucleotide sequences 5'-CTTCCCAGAAT-CAAGAACGGCTGTGTGCATTTAAAGATCCC-TACCAGCAAGACCTTGGG ATAGGT-GAGAGTAGAATCTCTCATGAAAATGGGACA-ATATTATGCTCCAAAGGTAGCAC ATGCTATGGTC-TATGGGAGAAATCAAAAGGGGACATCAATCTTGT-GAAACAAG-3' (SEQ. ID. NO: 2) of the $2^{nd}$ exon, 5'-GATGTTGGTCTCACATTGGCGATCCT-CAAGAGTGTCACTATGAAGAATGTGTAGTAACT ACTACCCCACCCTCAATTCAGAATGGAACAT-ACCGTTTTTGCTGCTGTAGTACAGATTT ATGTAATGTCAACTTTACTGAGAATTTTC-CACCTCCTGATACAACACCACTCA-3' (SEQ. ID. NO: 3) of the 3rd exon, 5'-GTCCACCTCATTCATT-TAATCGAGATGAGACAATAATCATTGCTTTGG-CATCAGTCTCT GTATTAGCTGTTTTGATAGTCGCCT-TATGTTTTGGATACAGAATGTTGACAG-3' (SEQ. ID. NO: 4) of the exon and 5'-GA-GACCGAAAACAAGGCCTTCACAGTATGAACAT-GATGGAAGCAGCGGCGTCAGAGCCT TCTCTGGACTTGGATAATCTGAAGCTGCTGGAG-3' (SEQ. ID. NO: 5) of the $5^{th}$ exon of the BMPRII gene. More precisely, the BMPRII gene knock out transgenic CHO cell line has been transfected with a vector comprising the nucleotide sequences represented by SEQ. ID. NO: 11, SEQ. ID. NO: 12 and SEQ. ID. NO: 13, so that the nucleotide sequences of the $2^{nd}$ to $5^{th}$ exons of the BMPRII gene have been mutated.

The CHO cell line above can be a DHFR (dihydrofolate reductase) gene knock out cell line. The expression of a target protein gene in the DHFR gene knock out CHO cell line can be amplified by using DHFR/MTX (dihydrofolate reductase/methotrexate) system. Particularly, a vector comprising the nucleotide sequence encoding DHFR and a target protein is introduced into the host cells in which DFHR gene necessary for cell growth is knocked-out. Then, the cells are treated with MTX suppressing DHFR gene expression to inhibit cell growth. At this time, the cells can amplify the expression of a gene encoding DHFR and a target protein in order to overcome the suppression above.

The present invention also provides a preparation method of a transgenic CHO cell line in which the BMP receptor gene BMPRIA or BMPRII is knocked-out. The preparation method comprises the following steps:

1) constructing a vector to knock-out the BMP receptor gene BMPRIA or BMPRII;

2) introducing the vector of step 1) into a CHO cell line; and 3) selecting the CHO cell line in which the BMP receptor gene BMPRIA or BMPRII has been knocked-out from those CHO cell lines introduced with the vector of step 2).

The said BMPRIA gene is a BMP type I receptor gene and the said BMPRII gene is a BMP type II receptor gene. Particularly, the BMPRIA gene of step 1) can have a mutation in the nucleotide sequence of the $2^{nd}$ exon of the BMPRIA gene. More particularly, the BMPRIA gene can have a mutation in the nucleotide sequence 5'-ATGCATGTGTTATTAATAGCATCATCTGGGCAGTGGCCTGAGCAGTAACACTTTAAGAAAGGCAAAGTATCCTCCGGGGCTAAAGTCACTCCATTTTCTGGCTTCTTCTGGTCCAAGT CTGATTTCATACCAGTACCATGGAGCATACTGTCTAGATTCTGCC-3' (SEQ. ID. NO: 1) of the $2^{nd}$ exon of the BMPRIA gene. In addition, the BMPRII gene of step 1) can have a mutation in the nucleotide sequences of the $2^{nd}$ to $5^{th}$ exons of the BMPRII gene. More particularly, the BMPRII gene can have a mutation in the nucleotide sequences 5'-CTTCCCAGAATCAAGAACGGCTGTGTGCATTTAAAGATCCCTACCAGCAAGACCTTGGG ATAGGTGAGAGTAGAATCTCTCATGAAAATGGGACAATATTATGCTCCAAAGGTAGCAC ATGCTATGGTCTATGGGAGAAATCAAAAGGGGACATCAATCTTGTGAAACAAG-3' (SEQ. ID. NO: 2) of the $2^{nd}$ exon, 5'-GATGTTGGTCTCACATTGGCGATCCTCAAGAGTGTCACTATGAAGAATGTGTAGTAACT ACTACCCCACCCTCAATTCAGAATGGAACATACCGTTTTTGCTGCTGTAGTACAGATTT ATGTAATGTCAACTTTACTGAGAATTTTCCACCTCCTGATACAACACCACTCA-3' (SEQ. ID. NO: 3) of the $3^{rd}$ exon, 5'-GTCCACCTCATTCATTTAATCGAGATGAGACAATAATCATTGCTTTGGCATCAGTCTCT GTATTAGCTGTTTTGATAGTCGCCTTATGTTTTGGATACAGAATGTTGACAG-3' (SEQ. ID. NO: 4) of the $4^{th}$ exon and 5'-GAGACCGAAAACAAGGCCTTCACAGTATGAACATGATGGAAGCAGCGGCGTCAGAGCCT TCTCTGGACTTGGATAATCTGAAGCTGCTGGAG-3' (SEQ. ID. NO: 5) of the $5^{th}$ exon of the BMPRII gene.

The vector of step 1) preferably includes gene scissors, and the gene scissors are preferably selected from the group consisting of ZFN (zinc-finger nuclease), TALEN (transcription activator-like effector nuclease) and CRISPR/Cas9 (clustered regularly interspaced short palindromic repeats/CRISPR-associated protein-9), but not always limited thereto. According to an example of the present invention, the vector can include CRISPR/Case9, and particularly the vector can be the one that can express sgRNA and Cas9 protein targeting the BMP receptor gene BMPRIA or BMPRII.

More particularly, the vector that can knock out the BMPRIA gene of step 1) can be a vector containing the nucleotide sequence of sgRNA targeting the $2^{nd}$ exon nucleotide sequence of BMPRIA gene or a vector containing the nucleotide sequence encoding Cas9 protein. According to an example of the present invention, the Cas9 protein is composed of the amino acid sequence represented by SEQ. ID. NO: 9. The nucleotide sequence of sgRNA targeting the $2^{nd}$ exon nucleotide sequence of BMPRIA gene can be 5'-GAAAGGCAAAGTATCCTCCGGGG-3' (SEQ. ID. NO: 6). More particularly, the vector that can knock out the BMPRIA gene of step 1) can be composed of the nucleotide sequence represented by SEQ. ID. NO: 10 or SEQ. ID. NO: 13.

The vector that can knock out the BMPRII gene of step 1) can be a vector comprising the nucleotide sequence of sgRNA targeting the $2^{nd}$ exon nucleotide sequence of BMPRII gene, a vector comprising the nucleotide sequence of sgRNA targeting the $5^{th}$ exon nucleotide sequence of BMPRII gene or a vector comprising the nucleotide sequence encoding Cas9 protein. The nucleotide sequence of sgRNA targeting the $2^{nd}$ exon nucleotide sequence of BMPRII gene can be 5'-GGGACAATATTATGCTCCAAAGG-3' (SEQ. ID. NO: 7). The nucleotide sequence of sgRNA targeting the $5^{th}$ exon nucleotide sequence of BMPRII gene can be 5'-AGCGGCGTCAGAGCCTTCTCTGG-3' (SEQ. ID. NO: 8). More particularly, the vector that can knock out the BMPRII gene of step 1) can be composed of the nucleotide sequence represented by SEQ. ID. NO: 11, SEQ. ID. NO: 12 or SEQ. ID. NO: 13.

A method for introducing the vector of step 2) into the CHO cell line is exemplified by transformation, transfection, electroporation, transduction, microinjection or ballistic introduction, but not always limited thereto. According to an example of the present invention, the vector of step 2) can be introduced into the CHO cell line via transformation using lipofectamine.

The CHO cell line of step 2) can be a DHFR gene knock out cell line. The expression of a target protein gene in the DHFR gene knock out CHO cell line can be amplified by using DHFR/MTX system.

In addition, the step of selecting the cell line in which the BMP receptor gene BMPRIA or BMPRII has been knocked-out in step 3) can be achieved by various methods informed to those in the art. For example, PCR using genomic DNA as a template or nucleotide sequencing can be used.

Figure 3:
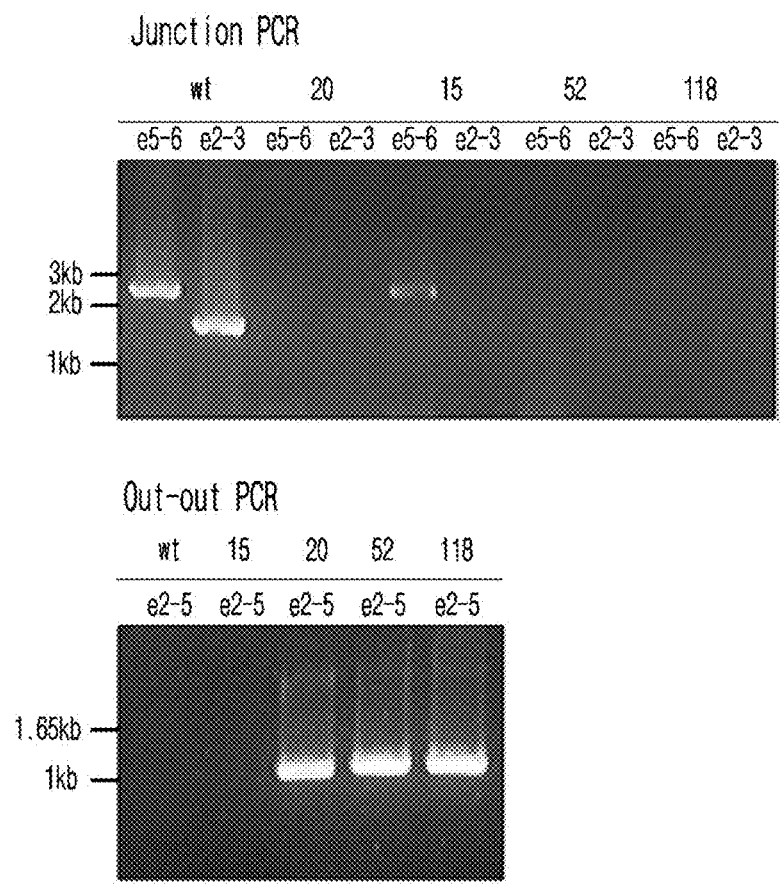
FIG. 3 is a set of photographs illustrating the results of junction PCR and out-out PCR to confirm the BMPRII gene knock-out clones (20, 52 and 118)
(wt: wild type;
e5-6: PCR with primers targeting exons 5 to 6;
e2-3: PCR with primers targeting exons 2 to 3;
e2-5: PCR with primers targeting exons 2 to 5).

In a preferred embodiment of the present invention, the present inventors introduced a vector expressing Cas 9 protein and sgRNA targeting BMPRIA gene or BMPRII gene in CHO host cells and then selected the cell line in which the BMPRIA gene or BMPRII gene was mutated or deleted in all homologous chromosome pairs in CHO cells (see FIGS. 1-3).

In addition, the present invention provides a production method of a target protein using a transgenic CHO cell line in which the BMP receptor gene BMPRIA or BMPRII is knocked-out. The production method of a target protein comprises the following steps:

1) introducing a vector containing the nucleotide sequence encoding a target protein into the transgenic CHO cell line in which the BMP receptor gene BMPRIA or BMPRII has been knocked-out;

2) culturing the cell line prepared in step 1) above; and 3) separating and purifying the target protein produced in step 2) above.

The transgenic CHO cell line in which the BMP receptor gene BMPRIA or BMPRII has been knocked-out of step 1) is as described above. According to an example of the present invention, the BMPRIA gene of step 1) can have a mutation in the nucleotide sequence of the $2^{nd}$ exon of the BMPRIA gene. More particularly, the BMPRIA gene can have a mutation in the nucleotide sequence 5'-ATG-CATGTGTTATTAATAGCATCATCTGGGCAGTGGCCT-GAGCAGTAACACTTTAAGAA AGGCAAAGTATCCTCCGGGGCTAAAGTCACTCCAT-TTTCTGGCTTCTTCTGGTCCAAGT CTGATTTCAT-ACCAGTACCATGGAGCATACTGTCTAGATTCTGCC-3' (SEQ. ID. NO: 1) of the $2^{nd}$ exon of the BMPRIA gene. In addition, the BMPRII gene of step 1) can have a mutation in the nucleotide sequences of the $2^{nd}$ to $5^{th}$ exons of the BMPRII gene. More particularly, the BMPRII gene can have a mutation in the nucleotide sequences 5'-CTTCCCAGAAT-CAAGAACGGCTGTGTGCATTTAAAGATCCC-TACCAGCAAGACCTTGGG ATAGGT-GAGAGTAGAATCTCTCATGAAAATGGGACAATA-TTATGCTCCAAAGGTAGCAC ATGCTATGGTC-TATGGGAGAAATCAAAAGGGGACATCAATCTTGT-GAAACAAG-3' (SEQ. ID. NO: 2) of the 2nd exon, 5'-GATGTTGGTCTCACATTGGCGATCCT-CAAGAGTGTCACTATGAAGAATGTGTAGTAACT ACTACCCCACCCTCAATTCAGAATGGAACAT-ACCGTTTTTGCTGCTGTAGTACAGATTT ATGTAATGTCAACTTTACTGAGAATTTTC-CACCTCCTGATACAACACCACTCA-3' (SEQ. ID. NO: 3) of the $3^{rd}$ exon, 5'-GTCCACCTCATTCATT-TAATCGAGATGAGACAATAATCATTGCTTTGG-CATCAGTCTCT GTATTAGCTGTTTTGATAGTCGCCT-TATGTTTTGGATACAGAATGTTGACAG-3' (SEQ. ID. NO: 4) of the $4^{th}$ exon and 5'-GA-GACCGAAAACAAGGCCTTCACAGTATGAACAT-GATGGAAGCAGCGGCGTCAGAGCCT TCTCTGGACTTGGATAATCTGAAGCTGCTGGAG-3' (SEQ. ID. NO: 5) of the $5^{th}$ exon of the BMPRII gene.

The CHO cell line of step 1) can be a DHFR gene knock out cell line. The expression of a target protein gene in the DHFR gene knock out CHO cell line can be amplified by using DHFR/MTX system. Particularly, a vector comprising the nucleotide sequence encoding DHFR and a target protein is introduced into the host cells in which DFHR gene necessary for cell growth is knocked-out. Then, the cells are treated with MTX suppressing DHFR gene expression to inhibit cell growth. At this time, the cells can amplify the expression of a gene encoding DHFR and a target protein in order to overcome the suppression above. So, the vector of step 1) can additionally include a nucleotide sequence encoding DHFR protein.

The target protein of step 1) can be any one selected from the group consisting of BMP2, BMP3, BMP4, BMPS, BMP6, BMP7, BMP8, BMP9, BMP10, BMP11, BMP12, BMP13, BMP14 and BMP15, but not always limited thereto.

A method for introducing the vector comprising the nucleotide sequence encoding the target protein of step 1) into the CHO cell line is exemplified by transformation, transfection, electroporation, transduction, microinjection or ballistic introduction, but not always limited thereto. According to an example of the present invention, the vector of step 1) can be introduced into the CHO cell line via transformation using lipofectamine.

The cell line of step 2) can be cultured by batch culture, fed-batch culture or continuous culture, but not always limited thereto. The culture in step 2) is preferably performed after treating MTX (methotrexate).

In a preferred embodiment of the present invention, the present inventors constructed a CHO cell line in which BMPRIA or BMPRII gene was knocked out, and introduced a vector comprising the nucleotide sequence encoding DHFR and BMP4 (recombinant human BMP4, rhBMP4) into the cell line. The cell line was treated with MTX, followed by culture. Then, rhBMP4 production was confirmed. As a result, it was confirmed that the growth of CHO cells in which BMPRIA or BMPRII gene was knocked out was increased and the production of rhBMP4 was higher than the wild type (see FIGS. 4-7).

Therefore, the BMP receptor gene knock out CHO cell line of the present invention can prevent the activation of intracellular signal transduction and self concentration control pathway to increase CHO cell growth, so that the productivity of a target protein to be produced can be improved using the cell line.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Construction of BMPRIA Gene Knock Out CHO Cell Line

To construct a BMPRIA gene knock out CHO cell line, CHO DG44 host cells were cultured in IMDM (Iscov's Modified Dulbecco's Medium) supplemented with 7% (v/v) dFBS (dialyzed fetal bovine serum) and hypoxanthine/thymidine (HT) via adhesion culture. A vector containing gene scissors targeting the $2^{nd}$ exon (SEQ. ID. NO: 1) of BMPRIA gene was introduced into the cultured CHO cells. Particularly, the said vector was the one expressing Cas9 protein (SEQ. ID. NO: 9) and sgRNA (SEQ. ID. NO: 6) targeting the $2^{nd}$ exon sequence of BMPRIA gene. The vector was prepared by Toolgene. The entire sequence of the constructed vector was identified as SEQ. ID. NO: 10 and SEQ. ID. NO: 13. The constructed vector was introduced into CHO cells using lipofectamine (lipofectamine 2000, Life technology).

Example 2: Construction of BMPRII Gene Knock Out CHO Cell Line

To construct a BMPRII gene knock out CHO cell line, cells were cultured by the same manner as described in Example 1. A vector containing gene scissors targeting the $2^{nd}$ to $5^{th}$ exons (SEQ. ID. NOs: 2-5) of BMPRII gene was introduced into the cultured CHO cells. Particularly, the said vector includes the nucleotide sequences expressing sgRNA (SEQ. ID. NO: 7) targeting the $2^{nd}$ exon sequence of BMPRII gene, sgRNA (SEQ. ID. NO: 8) targeting the $5^{th}$ exon sequence of BMPRII gene and Cas9 protein (SEQ. ID. NO: 9). Using the sgRNA targeting the $2^{nd}$ and $5^{th}$ exons of BMPRII gene, all of the genomic fragments between the $2^{nd}$ and $5^{th}$ exons of BMPRII gene were removed. The vector was prepared by Toolgene. The entire sequence of the constructed vector was identified as SEQ. ID. NO: 11, SEQ. ID. NO: 12 and SEQ. ID. NO: 13. The constructed vector was introduced into CHO cells using lipofectamine (lipofectamine 2000, Life technology).

TABLE A

| SEQ. ID. NO: | Gene or protein | Nucleotide Sequence (5'→3') or Amino acid sequence |
|---|---|---|
| 1 | 2$^{nd}$ exons of BMPRIA gene | ATGCATGTGTTATTAATAGCATCATCTGGGCAGTGGCCTGAGCAGTAACACTTTAAGAAAGGCAAAGTATCCTCCGGGGCTAAAGTCACTCCATTTTCTGGCTTCTTCTGGTCCAAGTCTGATTTCATACCAGTACCATGGAGCATACTGTCTAGATTCTGCC |
| 2 | 2$^{nd}$ exons of BMPRII gene | CTTCCCAGAATCAAGAACGGCTGTGTGCATTTAAAGATCCCTACCAGCAAGACCTTGGGATAGGTGAGAGTAGAATCTCTCATGAAAATGGGACAATATTATGCTCCAAAGGTAGCACATGCTATGGTCTATGGGAGAAATCAAAAGGGGACATCAATCTTGTGAAACAAG |
| 3 | 3$^{rd}$ exons of BMPRII gene | GATGTTGGTCTCACATTGGCGATCCTCAAGAGTGTCACTATGAAGAATGTGTAGTAACTACTACCCCACCCTCAATTCAGAATGGAACATACCGTTTTTGCTGCTGTAGTACAGATTTATGTAATGTCAACTTTACTGAGAATTTTCCACCTCCTGATACAACACCACTCA |
| 4 | 4$^{th}$ exons of BMPRII gene | GTCCACCTCATTCATTTAATCGAGATGAGACAATAATCATTGCTTTGGCATCAGTCTCTGTATTAGCTGTTTTGATAGTCGCCTTATGTTTTGGATACAGAATGTTGACAG |
| 5 | 5$^{th}$ exons of BMPRII gene | GAGACCGAAAACAAGGCCTTCACAGTATGAACATGATGGAAGCAGCGGCGTCAGAGCCTTCTCTGGACTTGGATAATCTGAAGCTGCTGGAG |
| 6 | sgRNA targeting the 2$^{nd}$ exon sequence of BMPRIA gene | GAAAGGCAAAGTATCCTCCGGGG |
| 7 | sgRNA targeting the 2$^{nd}$ exon sequence of BMPRII gene | GGGACAATATTATGCTCCAAAGG |
| 8 | sgRNA targeting the 5$^{th}$ exon sequence of BMPRIA gene | AGCGGCGTCAGAGCCTTCTCTGG |
| 9 | Cas protein | MDKKYSIGLDIGTNSVGWAVITDEYKVPSKKFKVLGNTDRHSIKKNLIGALLFDSGETAEATRLKRTARRRYTRRKNRICYLQEIFSNEMAKVDDSFEHRLEESELVEEDKKHERHPIEGNIVDEVAYHEKYPTIYHLRKKLVDSTDKADLRLIYLALAHMIKFRGHFLIEGDLNPDNSDVDKLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYADLFLAAKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNREDLLRKQRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVLPKHSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILEDIVLTLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHIANLAGSPAIKKGILQTVKVVDELVKVMGRHKPENIVIEMARENQTTQKGQKNSRERMKRIEEGIKELGSQILKEHPVENTQLQNEKLYLYYLQNGRDMYVDQELDINRLSDYDVDHIVPQSFLKDDSIDNKVLTRSDKNRGKSDNVPSEEVVKKMKNYWRQLLNAKLITQRKFDNLTKAERGGLSELDKAGFIKRQLVETRQITKHVAQILDSRMNTKYDENDKLIREVKVITLKSKLVSDFRKDFQFYKVREINNYHHAHDAYLNAVVGTALIKKYPKLESEFVYGDYKVYDVRKMIAKSEQEIGKATAKYFFYSNIMNFFKTEITLANGEIRKRPLIETNGETGEIVWDKGRDFATVRKVLSMPQVNIVKKTEVQTGGFSKESILPKRNSDKLIARKKDWDPKKYGGFDSPTVAYSVLVVAKVEKGKSKKLKSVKELLGITIMERSSFEKNPIDFLEAKGYKEVKKDLIIKLPKYSLFELENGRKRMLASAGELQKGNELALPSKYVNFLYLASHYEKLKGSPEDNEQKQLFVEQHKHYLDEIIEQISEFSKRVILADANLDKVLSAYNKHRDKPIREQAENIIHLFTLTNLGAPAAFKYFDTTIDRKRYTSTKEVLDATLIHQSITGLYETRIDLSQLGGD |
| 10 | A vector expressing sgRNA that targets the 2$^{nd}$ exon sequence of | gacgaagactcaattgtcgattagtgaacggatctcgacggtatcgatcacgagactagcctcgagcggccgcccccttcaccgagggcctatttcccatgattccttcatatttgcatatacgatacaaggctgttagagagataattggaattaatttgactgtaaacacaaagatattagtacaaatacgtgacgtagaaagtaataatttcttgggtagtttgcagttttaaatatgttttaaaatggactatcatatgcttaccgtaacttgaaagtatt |

TABLE A -continued

| SEQ. ID. NO: | Gene or protein | Nucleotide Sequence (5'→3') or Amino acid sequence |
|---|---|---|
| | BMPRIA gene | tcgatttcttggctttatatatcttgtggaaaggacgaaacaccgGAAAGGCAAAGTATCCTCCGGGGgttttagagctagaaatagcaagttaaa<br>ataaggctagtccgttatcaacttgaaaaagtggcaccgagtcggtgc<br>ttttttctagattcgcgatgtacgggccagatatacgcgttgacattg<br>attattgactagttgtcttcctgcattaatgaatcggccaacgcgcgg<br>ggagaggcggtttgcgtattgggcgctcttccgcttcctcgctcactg<br>actcgctgcgctcggtcgttcggctgcggcgagcggtatcagctcact<br>caaaggcggtaatacggttatccacagaatcaggggataacgcaggaa<br>agaacatgtgagcaaaaggccagcaaaaggccaggaaccgtaaaaagg<br>ccgcgttgctggcgttttccataggctccgcccccctgacgagcatc<br>acaaaaatcgacgctcaagtcagaggtggcgaaacccgacaggactat<br>aaagataccaggcgtttccccctggaagctccctcgtgcgctctcctg<br>ttccgaccctgccgcttaccggatacctgtccgcctttctcccttcgg<br>gaagcgtggcgctttctcaatgctcacgctgtaggtatctcagttcgg<br>tgtaggtcgttcgctccaagctgggctgtgtgcacgaaccccccgttc<br>agcccgaccgctgcgccttatccggtaactatcgtcttgagtccaacc<br>cggtaagacacgacttatcgccactggcagcagccactggtaacagga<br>ttagcagagcgaggtatgtaggcggtgctacagagttcttgaagtggt<br>ggcctaactacggctacactagaaggacagtatttggtatctcgcgctc<br>tgctgaagccagttaccttcggaaaaagagttggtagctcttgatccg<br>gcaaacaaaccaccgctggtagcggtggttttttgtttgcaagcagc<br>agattacgcgcagaaaaaaaggatctcaagaagatcctttgatctttt<br>ctacggggtctgacgctcagtggaacgaaaactcacgttaagggattt<br>tggtcatgagattatcaaaaaggatcttcacctagatccttttaaatt<br>aaaaatgaagttttaaatcaatctaaagtatatatgagtaaacttggt<br>ctgacagttaccaatgcttaatcagtgaggcacctatctcagcgatct<br>gtctatttcgttcatccatagttgcctgactccccgtcgtgtagataa<br>ctacgatacgggagggcttaccatctggccccagtgctgcaatgatac<br>cgcgagatccacgctcaccggctccagatttatcagcaataaaccagc<br>cagccggaagggccgagcgcagaagtggtcctgcaactttatccgcct<br>ccatccagtctattaattgttgccgggaagctagagtaagtagttcgc<br>cagttaatagtttgcgcaacgttgttgccattgctacaggcatcgtgg<br>tgtcacgctcgtcgtttggtatggcttcattcagctccggttcccaac<br>gatcaaggcgagttacatgatccccatgttgtgcaaaaaagcggtta<br>gctccttcggtcctccgatcgttgtcagaagtaagttggccgcagtgt<br>tatcactcatggttatggcagcactgcataattctcttactgtcatgc<br>catccgtaagatgcttttctgtgactggtgagtactcaaccaagtcat<br>tctgagaatagtgtatgcggcgaccgagttgctcttgcccggcgtcaa<br>tacgggataataccgcgccacatagcagaactttaaaagtgctcatca<br>ttggaaaacgttcttcggggcgaaaactctcaaggatcttaccgctgt<br>tgagatccagttcgatgtaacccactcgtgcacccaactgatcttcag<br>catcttttactttcaccagcgtttctgggtgagcaaaaacaggaaggc<br>aaaatgccgcaaaaaagggaataagggcgacacggaaatgttgaatac<br>tcatactcttcctttttcaatattattgaagcatttatcagggttatt<br>gtctcatgagcggatacatatttgaatgtatttagaaaaataaacaaa<br>tagggggttccgcgcacatttccccgaaaagtgccacctgacgtc |
| 11 | A vector expressing sgRNA that targets the 2<sup>nd</sup> exon sequence of BMPRII gene | gacgaagactcaattgtcgattagtgaacggatctcgacggtatcgat<br>cacgagactagcctcgagcggccgcccccttcaccgagggcctatttc<br>ccatgattccttcatatttgcatatacgatacaaggctgttagagaga<br>taattggaattaatttgactgtaaacacaaagatattagtacaaaata<br>cgtgacgtagaaagtaataatttcttgggtagtttgcagttttaaat<br>tatgttttaaaatggactatcatatgcttaccgtaacttgaaagtatt<br>tcgatttcttggctttatatatcttgtggaaaggacgaaacaccgGGGACAATATTATGCTCCAAAGGgttttagagctagaaatagcaagttaaa<br>ataaggctagtccgttatcaacttgaaaaagtggcaccgagtcggtgc<br>ttttttctagattcgcgatgtacgggccagatatacgcgttgacattg<br>attattgactagttgtcttcctgcattaatgaatcggccaacgcgcgg<br>ggagaggcggtttgcgtattgggcgctcttccgcttcctcgctcactg<br>actcgctgcgctcggtcgttcggctgcggcgagcggtatcagctcact<br>caaaggcggtaatacggttatccacagaatcaggggataacgcaggaa<br>agaacatgtgagcaaaaggccagcaaaaggccaggaaccgtaaaaagg<br>ccgcgttgctggcgttttccataggctccgcccccctgacgagcatc<br>acaaaaatcgacgctcaagtcagaggtggcgaaacccgacaggactat<br>aaagataccaggcgtttccccctggaagctccctcgtgcgctctcctg<br>ttccgaccctgccgcttaccggatacctgtccgcctttctcccttcgg<br>gaagcgtggcgctttctcaatgctcacgctgtaggtatctcagttcgg<br>tgtaggtcgttcgctccaagctgggctgtgtgcacgaaccccccgttc<br>agcccgaccgctgcgccttatccggtaactatcgtcttgagtccaacc<br>cggtaagacacgacttatcgccactggcagcagccactggtaacagga<br>ttagcagagcgaggtatgtaggcggtgctacagagttcttgaagtggt<br>ggcctaactacggctacactagaaggacagtatttggtatctcgcgctc<br>tgctgaagccagttaccttcggaaaaagagttggtagctcttgatccg<br>gcaaacaaaccaccgctggtagcggtggttttttgtttgcaagcagc<br>agattacgcgcagaaaaaaaggatctcaagaagatcctttgatctttt<br>ctacggggtctgacgctcagtggaacgaaaactcacgttaagggattt |

TABLE A -continued

| SEQ. ID. NO: | Gene or protein | Nucleotide Sequence (5'→3') or Amino acid sequence |
|---|---|---|
| | | tggtcatgagattatcaaaaaggatcttcacctagatcctttaaatt aaaaatgaagttttaaatcaatctaaagtatatatgagtaaacttggt ctgacagttaccaatgcttaatcagtgaggcacctatctcagcgatct gtctatttcgttcatccatagttgcctgactccccgtcgtgtagataa ctacgatacgggagggcttaccatctggccccagtgctgcaatgatac cgcgagatccacgctcaccggctccagatttatcagcaataaaccagc cagccggaagggccgagcgcagaagtggtcctgcaactttatccgcct ccatccagtctattaattgttgccgggaagctagagtaagtagttcgc cagttaatagtttgcgcaacgttgttgccattgctacaggcatcgtgg tgtcacgctcgtcgtttggtatggcttcattcagctccggttcccaac gatcaaggcgagttacatgatcccccatgttgtgcaaaaaagcggtta gctccttcggtcctccgatcgttgtcagaagtaagttggccgcagtgt tatcactcatggttatggcagcactgcataattctcttactgtcatgc catccgtaagatgcttttctgtgactggtgagtactcaaccaagtcat tctgagaatagtgtatgcggcgaccgagttgctcttgcccggcgtcaa tacgggataataccgcgccacatagcagaactttaaaagtgctcatca ttggaaaacgttcttcggggcgaaaactctcaaggatcttaccgctgt tgagatccagttcgatgtaacccactcgtgcacccaactgatcttcag catctttactttcaccagcgtttctgggtgagcaaaaacaggaaggc aaaatgccgcaaaaagggaataagggcgcacggaaatgttgaatac tcatactcttcctttttcaatattattgaagcatttatcagggttatt gtctcatgagcggatacatatttgaatgtatttagaaaaataaacaaa taggggttccgcgcacatttccccgaaaagtgccacctgacgtc |
| 12 | A vector expressing sgRNA that targets the 5th exon sequence of BMPRII gene | gacgaagactcaattgtcgattagtgaacggatctcgacggtatcgat cacgagactagcctcgagcggccgcccccttcaccgagggcctatttc ccatgattccttcatatttgcatatacgatacaaggctgttagagaga taattggaattaatttgactgtaaacacaaagatattagtacaaaata cgtgacgtagaaagtaataattcttgggtagtttgcagttttaaat tatgtttaaaatggactatcatatgcttaccgtaacttgaaagtatt tcgatttcttggcttatatatcttgtggaaaggacgaaacaccgAGC GGCGTCAGAGCCTTCTCTGGgttttagagctagaaatagcaagttaaa ataaggctagtccgttatcaacttgaaaaagtggcaccgagtcggtgc ttttttctagattcgcgatgtacgggccagatatacgcgttgacattg attattgactagttgtcttcctgcattaatgaatcggccaacgcgcgg ggagaggcggtttgcgtattgggcgctcttccgcttcctcgctcactg actcgctgcgctcggtcgttcggctgcggcgagcggtatcagctcact caaaggcggtaatacggttatccacagaatcaggggataacgcaggaa agaacatgtgagcaaaaggccagcaaaaggccaggaaccgtaaaaagg ccgcgttgctggcgtttttccataggctccgcccccctgacgagcatc acaaaaatcgacgctcaagtcagaggtggcgaaacccgacaggactat aaagataccaggcgtttccccctggaagctccctcgtgcgctctcctg ttccgaccctgccgcttaccggatacctgtccgcctttctcccttcgg gaagcgtggcgctttctcaatgctcacgctgtaggtatctcagttcgg tgtaggtcgttcgctccaagctgggctgtgtgcacgaaccccccgttc agcccgaccgctgcgccttatccggtaactatcgtcttgagtccaacc cggtaagacacgacttatcgccactggcagcagccactggtaacagga ttagcagagcgaggtatgtaggcggtgctacagagttcttgaagtggt ggcctaactacggctacactagaaggacagtatttggtatctgcgctc tgctgaagccagttaccttcggaaaaagagttggtagctcttgatccg gcaaacaaaccaccgctggtagcggtggtttttttgtttgcaagcagc agattacgcgcagaaaaaaaggatctcaagaagatcctttgatcttt ctacggggtctgacgctcagtggaacgaaaactcacgttaagggattt tggtcatgagattatcaaaaaggatcttcacctagatccttttaaatt aaaaatgaagttttaaatcaatctaaagtatatatgagtaaacttggt ctgacagttaccaatgcttaatcagtgaggcacctatctcagcgatct gtctatttcgttcatccatagttgcctgactccccgtcgtgtagataa ctacgatacgggagggcttaccatctggccccagtgctgcaatgatac cgcgagatccacgctcaccggctccagatttatcagcaataaaccagc cagccggaagggccgagcgcagaagtggtcctgcaactttatccgcct ccatccagtctattaattgttgccgggaagctagagtaagtagttcgc cagttaatagtttgcgcaacgttgttgccattgctacaggcatcgtgg tgtcacgctcgtcgtttggtatggcttcattcagctccggttcccaac gatcaaggcgagttacatgatcccccatgttgtgcaaaaaagcggtta gctccttcggtcctccgatcgttgtcagaagtaagttggccgcagtgt tatcactcatggttatggcagcactgcataattctcttactgtcatgc catccgtaagatgcttttctgtgactggtgagtactcaaccaagtcat tctgagaatagtgtatgcggcgaccgagttgctcttgcccggcgtcaa tacgggataataccgcgccacatagcagaactttaaaagtgctcatca ttggaaaacgttcttcggggcgaaaactctcaaggatcttaccgctgt tgagatccagttcgatgtaacccactcgtgcacccaactgatcttcag catctttactttcaccagcgtttctgggtgagcaaaaacaggaaggc aaaatgccgcaaaaagggaataagggcgcacggaaatgttgaatac tcatactcttcctttttcaatattattgaagcatttatcagggttatt gtctcatgagcggatacatatttgaatgtatttagaaaaataaacaaa taggggttccgcgcacatttccccgaaaagtgccacctgacgtc |

TABLE A -continued

| SEQ. ID. NO: | Gene or protein | Nucleotide Sequence (5'→3') or Amino acid sequence |
|---|---|---|
| 13 | A vector expressing Cas protein | GACGGATCGGGAGATCTCCCGATCCCCTATGGTCGACTCTCAGTACAA TCTGCTCTGATGCCGCATAGTTAAGCCAGTATCTGCTCCCTGCTTGTG TGTTGGAGGTCGCTGAGTAGTGCGCGAGCAAAATTTAAGCTACAACAA GGCAAGGCTTGACCGACAATTGCATGAAGAATCTGCTTAGGGTTAGGC GTTTTGCGCTGCTTCGCGATGTACGGGCCAGATATACGCGTTGACATT GATTATTGACTAGTTATTAATAGTAATCAATTACGGGGTCATTAGTTC ATAGCCCATATATGGAGTTCCGCGTTACATAACTTACGGTAAATGGCC CGCCTGGCTGACCGCCCAACGACCCCCGCCCATTGACGTCAATAATGA CGTATGTTCCCATAGTAACGCCAATAGGGACTTTCCATTGACGTCAAT GGGTGGACTATTTACGGTAAACTGCCCACTTGGCAGTACATCAAGTGT ATCATATGCCAAGTACGCCCCCTATTGACGTCAATGACGGTAAATGGC CCGCCTGGCATTATGCCCAGTACATGACCTTATGGGACTTTCCTACTT GGCAGTACATCTACGTATTAGTCATCGCTATTACCATGGTGATGCGGT TTTGGCAGTACATCAATGGGCGTGGATAGCGGTTTGACTCACGGGGAT TTCCAAGTCTCCACCCCATTGACGTCAATGGGAGTTTGTTTTGGCACC AAAATCAACGGGACTTTCCAAAATGTCGTAACAACTCCGCCCCATTGA CGCAAATGGGCGGTAGGCGTGTACGGTGGGAGGTCTATATAAGCAGAG CTCTCTGGCTAACTAGAGAACCCACTGCTTACTGGCTTATCGAAATTA ATACGACTCACTATAGGGAGACCCAAGCTTGCCACCATGGACAAGAAG TACAGCATCGGCCTGGACATCGGTACCAACAGCGTGGGCTGGGCCGTG ATCACCGACGAGTACAAGGTGCCCAGCAAGAAGTTCAAGGTGCTGGGC AACACCGACCGCCACAGCATCAAGAAGAACCTGATCGGCGCCCTGCTG TTCGACAGCGGCGAGACCGCCGAGGCCACCCGCCTGAAGCGCACCGCC CGCCGCCGCTACACCCGCCGCAAGAACCGCATCTGCTACCTGCAGGAG ATCTTCAGCAACGAGATGGCCAAGGTGGACGACAGCTTCTTCCACCGC CTGGAGGAGAGCTTCCTGGTGGAGGAGGACAAGAAGCACGAGCGCCAC CCCATCTTCGGCAACATCGTGGACGAGGTGGCCTACCACGAGAAGTAC CCCACCATCTACCACCTGCGCAAGAAGCTGGTGGACAGCACCGACAAG GCCGACCTGCGCCTGATCTACCTGGCCCTGGCCCACATGATCAAGTTC CGCGGCCACTTCCTGATCGAGGGCGACCTGAACCCCGACAACAGCGAC GTGGACAAGCTGTTCATCCAGCTGGTGCAGACCTACAACCAGCTGTTC GAGGAGAACCCCATCAACGCCAGCGGCGTGGACGCCAAGGCCATCCTG AGCGCCCGCCTGAGCAAGAGCCGCCGCCTGGAGAACCTGATCGCCCAG CTGCCCGGCGAGAAGAAGAACGGCCTGTTCGGCAACCTGATCGCCCTG AGCCTGGGCCTGACCCCCAACTTCAAGAGCAACTTCGACCTGGCCGAG GACGCCAAGCTGCAGCTGAGCAAGGACACCTACGACGACGACCTGGAC AACCTGCTGGCCCAGATCGGCGACCAGTACGCCGACCTGTTCCTGGCC GCCAAGAACCTGAGCGACGCCATCCTGCTGAGCGACATCCTGCGCGTG AACACCGAGATCACCAAGGCCCCCCTGAGCGCCAGCATGATCAAGCGC TACGACGAGCACCACCAGGACCTGACCCTGCTGAAGGCCCTGGTGCGC CAGCAGCTGCCCGAGAAGTACAAGGAGATCTTCTTCGACCAGAGCAAG AACGGCTACGCCGGCTACATCGACGGCGGCGCCAGCCAGGAGGAGTTC TACAAGTTCATCAAGCCCATCCTGGAGAAGATGGACGGCACCGAGGAG CTGCTGGTGAAGCTGAACCGCGAGGACCTGCTGCGCAAGCAGCGCACC TTCGACAACGGCAGCATCCCCCACCAGATCCACCTGGGCGAGCTGCAC GCCATCCTGCGCCGCCAGGAGGACTTCTACCCCTTCCTGAAGGACAAC CGCGAGAAGATCGAGAAGATCCTGACCTTCCGCATCCCCTACTACGTG GGCCCCCTGGCCCGCGGCAACAGCCGCTTCGCCTGGATGACCCGCAAG AGCGAGGAGACCATCACCCCCTGGAACTTCGAGGAGGTGGTGGACAAG GGCGCCAGCGCCCAGAGCTTCATCGAGCGCATGACCAACTTCGACAAG AACCTGCCCAACGAGAAGGTGCTGCCCAAGCACAGCCTGCTGTACGAG TACTTCACCGTGTACAACGAGCTGACCAAGGTGAAGTACGTGACCGAG GGCATGCGCAAGCCCGCCTTCCTGAGCGGCGAGCAGAAGAAGGCCATC GTGGACCTGCTGTTCAAGACCAACCGCAAGGTGACCGTGAAGCAGCTG AAGGAGGACTACTTCAAGAAGATCGAGTGCTTCGACAGCGTGGAGATC AGCGGCGTGGAGGACCGCTTCAACGCCAGCCTGGGCACCTACCACGAC CTGCTGAAGATCATCAAGGACAAGGACTTCCTGGACAACGAGGAGAAC GAGGACATCCTGGAGGACATCGTGCTGACCCTGACCCTGTTCGAGGAC CGCGAGATGATCGAGGAGCGCCTGAAGACCTACGCCCACCTGTTCGAC GACAAGGTGATGAAGCAGCTGAAGCGCCGCCGCTACACCGGCTGGGGC CGCCTGAGCCGCAAGCTTATCAACGGCATCCGCGACAAGCAGAGCGGC AAGACCATCCTGGACTTCCTGAAGAGCGACGGCTTCGCCAACCGCAAC TTCATGCAGCTGATCCACGACGACAGCCTGACCTTCAAGGAGGACATC CAGAAGGCCCAGGTGAGCGGCCAGGGCGACAGCCTGCACGAGCACATC GCCAACCTGGCCGGCAGCCCCGCCATCAAGAAGGGCATCCTGCAGACC GTGAAGGTGGTGGACGAGCTGGTGAAGGTGATGGGCCGCCACAAGCCC GAGAACATCGTGATCGAGATGGCCCGCGAGAACCAGACCACCCAGAAG GGCCAGAAGAACAGCCGCGAGCGCATGAAGCGCATCGAGGAGGGCATC AAGGAGCTGGGCAGCCAGATCCTGAAGGAGCACCCCGTGGAGAACACC CAGCTGCAGAACGAGAAGCTGTACCTGTACTACCTGCAGAACGGCCGC GACATGTACGTGGACCAGGAGCTGGACATCAACCGCCTGAGCGACTAC GACGTGGACCACATCGTGCCCCAGAGCTTCCTGAAGGACGACAGCATC GACAACAAGGTGCTGACCCGCAGCGACAAGAACCGCGGCAAGAGCGAC AACGTGCCCAGCGAGGAGGTGGTGAAGAAGATGAAGAACTACTGGCGC CAGCTGCTGAACGCCAAGCTGATCACCCAGCGCAAGTTCGACAACCTG |

TABLE A -continued

| SEQ. ID. NO: | Gene or protein | Nucleotide Sequence (5'→3') or Amino acid sequence |
|---|---|---|
| | | ACCAAGGCCGAGCGCGGCGGCCTGAGCGAGCTGGACAAGGCCGGCTTC
ATCAAGCGCCAGCTGGTGGAGACCCGCCAGATCACCAAGCACGTGGCC
CAGATCCTGGACAGCCGCATGAACACCAAGTACGACGAGAACGACAAG
CTGATCCGCGAGGTGAAGGTGATCACCCTGAAGAGCAAGCTGGTGAGC
GACTTCCGCAAGGACTTCCAGTTCTACAAGGTGCGCGAGATCAACAAC
TACCACCACGCCCACGACGCCTACCTGAACGCCGTGGTGGGCACCGCC
CTGATCAAGAAGTACCCCAAGCTGGAGAGCGAGTTCGTGTACGGCGAC
TACAAGGTGTACGACGTGCGCAAGATGATCGCCAAGAGCGAGCAGGAG
ATCGGCAAGGCCACCGCCAAGTACTTCTTCTACAGCAACATCATGAAC
TTCTTCAAGACCGAGATCACCCTGGCCAACGGCGAGATCCGCAAGCGC
CCCCTGATCGAGACCAACGGCGAGACCGGCGAGATCGTGTGGGACAAG
GGCCGCGACTTCGCCACCGTGCGCAAGGTGCTGAGCATGCCCCAGGTG
AACATCGTGAAGAAGACCGAGGTGCAGACCGGCGGCTTCAGCAAGGAG
AGCATCCTGCCCAAGCGCAACAGCGACAAGCTGATCGCCCGCAAGAAG
GACTGGGACCCCAAGAAGTACGGCGGCTTCGACAGCCCCACCGTGGCC
TACAGCGTGCTGGTGGTGGCCAAGGTGGAGAAGGGCAAGAGCAAGAAG
CTGAAGAGCGTGAAGGAGCTGCTGGGCATCACCATCATGGAGCGCAGC
AGCTTCGAGAAGAACCCCATCGACTTCCTGGAGGCCAAGGGCTACAAG
GAGGTGAAGAAGGACCTGATCATCAAGCTGCCCAAGTACAGCCTGTTC
GAGCTGGAGAACGGCCGCAAGCGCATGCTGGCCAGCGCCGGCGAGCTG
CAGAAGGGCAACGAGCTGGCCCTGCCCAGCAAGTACGTGAACTTCCTG
TACCTGGCCAGCCACTACGAGAAGCTGAAGGGCAGCCCCGAGGACAAC
GAGCAGAAGCAGCTGTTCGTGGAGCAGCACAAGCACTACCTGGACGAG
ATCATCGAGCAGATCAGCGAGTTCAGCAAGCGCGTGATCCTGGCCGAC
GCCAACCTGGACAAGGTGCTGAGCGCCTACAACAAGCACCGCGACAAG
CCCATCCGCGAGCAGGCCGAGAACATCATCCACCTGTTCACCCTGACC
AACCTGGGCGCCCCCGCCGCCTTCAAGTACTTCGACACCACCATCGAC
CGCAAGCGCTACACCAGCACCAAGGAGGTGCTGGACGCCACCCTGATC
CACCAGAGCATCACCGGTCTGTACGAGACCCGCATCGACCTGAGCCAG
CTGGGCGGCGACGGCGGCTCCGGACCTCCAAAGAAAAAGAGAAAAGTA
TACCCCTACGACGTGCCCGACTACGCCTAATAACTCGAGCATGCATCT
AGAGGGCCCTATTCTATAGTGTCACCTAAATGCTAGAGCTCGCTGATC
AGCCTCGACTGTGCCTTCTAGTTGCCAGCCATCTGTTGTTTGCCCCTC
CCCCGTGCCTTCCTTGACCCTGGAAGGTGCCACTCCCACTGTCCTTTC
CTAATAAAATGAGGAAATTGCATCGCATTGTCTGAGTAGGTGTCATTC
TATTCTGGGGGGTGGGGTGGGCAGGACAGCAAGGGGGAGGATTGGGA
AGACAATAGCAGGCATGCTGGGGATGCGGTGGGCTCTATGGCTTCTGA
GGCGGAAAGAACCAGCTGCATTAATGAATCGGCAACGCGCGGGGAGA
GGCGGTTTGCGTATTGGGCGCTCTTCCGCTTCCTCGCTCACTGACTCG
CTGCGCTCGGTCGTTCGGCTGCGGCGAGCGGTATCAGCTCACTCAAAG
GCGGTAATACGGTTATCCACAGAATCAGGGGATAACGCAGGAAAGAAC
ATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAA
AATCGACGCTCAAGTCAGAGGTGGCGAAACCCGACAGGACTATAAAGA
TACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGC
GTGGCGCTTTCTCAATGCTCACGCTGTAGGTATCTCAGTTCGGTGTAG
GTCGTTCGCTCCAAGCTGGGCTGTGTGCACGAACCCCCCGTTCAGCCC
GACCGCTGCGCCTTATCCGGTAACTATCGTCTTGAGTCCAACCCGGTA
AGACACGACTTATCGCCACTGGCAGCAGCCACTGGTAACAGGATTAGC
AGAGCGAGGTATGTAGGCGGTGCTACAGAGTTCTTGAAGTGGTGGCCT
AACTACGGCTACACTAGAAGGACAGTATTTGGTATCTGCGCTCTGCTG
AAGCCAGTTACCTTCGGAAAAAGAGTTGGTAGCTCTTGATCCGGCAAA
CAAACCACCGCTGGTAGCGGTGGTTTTTTTGTTTGCAAGCAGCAGATT
ACGCGCAGAAAAAAAGGATCTCAAGAAGATCCTTTGATCTTTTCTACG
GGGTCTGACGCTCAGTGGAACGAAAACTCACGTTAAGGGATTTTGGTC
ATGAGATTATCAAAAAGGATCTTCACCTAGATCCTTTTAAATTAAAAA
TGAAGTTTTAAATCAATCTAAAGTATATATGAGTAAACTTGGTCTGAC
AGTTACCAATGCTTAATCAGTGAGGCACCTATCTCAGCGATCTGTCTA
TTTCGTTCATCCATAGTTGCCTGACTCCCCGTCGTGTAGATAACTACG
ATACGGGAGGGCTTACCATCTGGCCCCAGTGCTGCAATGATACCGCGA
GACCCACGCTCACCGGCTCCAGATTTATCAGCAATAAACCAGCCAGCC
GGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTT
AATAGTTTGCGCAACGTTGTTGCCATTGCTACAGGCATCGTGGTGTCA
CGCTCGTCGTTTGGTATGGCTTCATTCAGCTCCGGTTCCCAACGATCA
AGGCGAGTTACATGATCCCCCATGTTGTGCAAAAAAGCGGTTAGCTCC
TTCGGTCCTCCGATCGTTGTCAGAAGTAAGTTGGCCGCAGTGTTATCA
CTCATGGTTATGGCAGCACTGCATAATTCTCTTACTGTCATGCCATCC
GTAAGATGCTTTTCTGTGACTGGTGAGTACTCAACCAAGTCATTCTGA
GAATAGTGTATGCGGCGACCGAGTTGCTCTTGCCCGGCGTCAATACGG
GATAATACCGCGCCACATAGCAGAACTTTAAAAGTGCTCATCATTGGA
AAACGTTCTTCGGGGCGAAAACTCTCAAGGATCTTACCGCTGTTGAGA
TCCAGTTCGATGTAACCCACTCGTGCACCCAACTGATCTTCAGCATCT
TTTACTTTCACCAGCGTTTCTGGGTGAGCAAAAACAGGAAGGCAAAAT
GCCGCAAAAAAGGGAATAAGGGCGACACGGAAATGTTGAATACTCATA |

TABLE A -continued

| SEQ. ID. NO: | Gene or protein | Nucleotide Sequence (5'→3') or Amino acid sequence |
|---|---|---|
| | | CTCTTCCTTTTTCAATATTATTGAAGCATTTATCAGGGTTATTGTCTC ATGAGCGGATACATATTTGAATGTATTTAGAAAAATAAACAAATAGGG GTTCCGCGCACATTTCCCCGAAAAGTGCCACCTGACGTC |

Experimental Example 1: Selection of BMPRIA or BMPRII Gene Knock Out CHO Cell Clone <1-1>Selection of BMPRIA Knock Out Clone To select BMPRIA gene knock out clones, DNA was extracted from the CHO host cells prepared in Example 1, followed by PCR.

Particularly, the vector comprising gene scissors constructed in Example 1 was introduced into the CHO host cells. 2 days later, the CHO cells were inoculated in a 96 well plate at the density of 0.3 cells/well, followed by culture for 10-14 days. At this time, IMDM (Iscov's Modified Dulbecco's Medium) supplemented with 7% (v/v) dFBS (dialyzed fetal bovine serum) and hypoxanthine/thymidine (HT) was used as the medium. From the cultured cells, gDNA was extracted, followed by PCR to confirm that BMPRIA gene was knocked out. PCR was performed using the extracted gDNA as a template with the primers listed in Table 2 and Primestar (Takara) products according to the conditions shown in Table 3 below. Gene sequence of the PCR product was confirmed by DNA Sanger sequencing.

As a result, 6 BMPRIA knock out clones were selected. Particularly, compared with the wild type, clones #22, #35, #43, #47, #61 and #68 were confirmed to have deletions or additions of one or more nucleotide sequences in the 2$^{nd}$ exon of BMPRIA gene (FIG. 2 and Table 4). In FIG. 2, blue color indicates the 2$^{nd}$ exon sequence of BMPRIA gene which is the target to be knocked-out, green color indicates PAM nucleotide sequence and red color indicates deletions or additions of nucleotide sequences from the target gene.

TABLE 2

| Target gene | Primer | Sequence (5'→3') |
|---|---|---|
| BMPRIA gene 2$^{nd}$ exon | Forward primer | GGAACTCACTCTGTAGAAGAGG (SEQ. ID. NO: 14) |
| | Reverse primer | GTGTTGGGGCACCCTTTGATC (SEQ. ID. NO: 15) |

TABLE 3

| Temperature | Time | Cycle |
|---|---|---|
| 95° C. | 2 min | 1 |
| 95° C. | 30 sec | 10 |
| 65° C. (−1° C./cycle) | 1 min | |
| 72° C. | 1 min 30 sec | |
| 95° C. | 30 sec | 30 |
| 55° C. | 1 min | |
| 72° C. | 1 min 30 sec | |
| 72° C. | 10 min | |

TABLE 4

| SEQ. ID. NO: | BMPRIA KO clone # | | Nucleotide sequence (5'-3') |
|---|---|---|---|
| SEQ. ID. NO: 24 | #22 | Δ17 | AGTAACACTTTAAGAAAGGCTAAAGTCACTCCATT |
| SEQ. ID. NO: 25 | | Δ4 | AGTAACACTTTAAGAAAGGCAAAGTTCCGGGGCTA AAGTCACTCCATT |
| SEQ. ID. NO: 26 | | +1 | AGTAACACTTTAAGAAAGGCAAAGTATCCTTCCGG GGCTAAAGTCACTCCATT |
| SEQ. ID. NO: 27 | #35 | Δ2 | AGTAACACTTTAAGAAAGGCAAAGTATTCCGGGGC TAAAGTCACTCCATT |
| SEQ. ID. NO: 28 | | Δ4 | AGTAACACTTTAAGAAAGGCAAAGTACCGGGGCTA AAGTCACTCCATT |
| SEQ. ID. NO: 29 | | +1 | AGTAACACTTTAAGAAAGGCAAAGTATCCTTCCGG GGCTAAAGTCACTCCATT |
| SEQ. ID. NO: 30 | | +2 | AGTAACACTTTAAGAAAGGCAAAGTATCCTTTCCG GGGCTAAAGTCACTCCATT |
| SEQ. ID. NO: 31 | #43 | +1 | AGTAACACTTTAAGAAAGGCAAAGTATCCTTCCGG GGCTAAAGTCACTCCATT |
| SEQ. ID. NO: 32 | #47 | Δ35 | AGTAAAGTCACTCCATT |
| SEQ. ID. NO: 33 | | Δ3, +1 | AGTAACACTTTAAGAAAGGCAAAGTATACCGGGGC TAAAGTCACTCCATT |
| SEQ. ID. NO: 34 | #61 | +115 | AGTAACACTTTAAGAAAGGCAAAGTATCCTCAGAC CATCCTGGACTTCCTGAAGAGCGACGGCTTCGCCA ACCGCAACTTCATGCAGCTGATCCACGACGACAGC CTGACCTTCAAGGAGGACATCCAGAAGGCCCAGGT GAGCGTCGGGGCTAAAGTCACTCCATT |
| SEQ. ID. NO: 35 | #68 | +49 | AGTAACACTTTAAGAAAGGCAAAGTATCCTCTGGT CTTGGAACACTTCCAAATCTCAGTGAAAAGCGAAG CCAGTGTTTCCGGGGCTAAAGTCACTCCATT |

<1-2>Selection of BMPRII Knock Out Clone

To select BMPRII gene knock out clones, DNA was extracted from the CHO host cells prepared in Example 1, followed by PCR.

Particularly, the host cells prepared in Example 2 were cultured and gDNA was extracted by the same manner as described in Experimental Example <1-1>. To confirm the knockout clones, junction PCR and out-out PCR were performed. Junction PCR is a kind of PCR performed with the primers targeting the non-knocked-out region and the knock-out region. In this PCR, when a gene is knocked-out, PCR product does not appear on gel. Out-out PCR is a kind of PCR performed with the primers targeting both sides of the knocked-out region. In this PCR, when a gene is knocked-out, a smaller sized PCR product appears on gel, compared with when a gene is not knocked-out. Primers used for the junction PCR and out-out PCR above are shown in Table 5 below.

As a result, 3 BMPRII gene knock out clones were selected. Particularly, junction PCR product and out-out PCR product were electrophoresed. As a result, compared with the wild type, bands of clones #20, #52 and #118 were not observed on junction PCR gel, while the bands were observed on out-out PCR gel (FIG. 3).

TABLE 5

| PCR | Target gene | Primer | Sequence (5'→3') |
|---|---|---|---|
| Junction PCR | $2^{nd}$-$3^{rd}$ exons of BMPRII gene | Forward primer | AGAACGGCTGTGTGCATTTA (SEQ. ID. NO: 16) |
| | | Reverse primer | CCAATGTGAGACCAACATCCT (SEQ. ID. NO: 17) |
| | $5^{th}$-$6^{th}$ exons of BMPRII gene | Forward primer | CTGCTGCAGCTCTTCTTAACT (SEQ. ID. NO: 18) |
| | | Reverse primer | CGCTCATCCAAGGAACCTTTA (SEQ. ID. NO: 19) |
| Out-out PCR | Genome between $1^{st}$ and $2^{nd}$ exon of BMPRII gene and genome between $5^{th}$ and $6^{th}$ exon of BMPRII gene | Forward primer | CTAACTCACAGAGATTGCCTACC (SEQ. ID. NO: 20) |
| | | Reverse primer | CCCAGCTCCTCCACTTTATTT (SEQ. ID. NO: 21) |

Experimental Example 2: Target Protein Production in BMPRIA or BMPRII Gene Knock Out CHO Cell Line To evaluate the productivity of a target protein in the BMPRIA or BMPRII gene knock out CHO host cell line selected in Experimental Example <1-2>, the target protein rhBMP4 (recombinant human BMP4) expression was induced in each CHO cell line, and then compared with that of the wild type CHO cell line.

First, the wild type CHO host cell line, the BMPRIA knock out CHO host cell lines and the BMPRII knock out CHO host cell lines selected in Experimental Example 1 were cultured in IMDM (Iscov's Modified Dulbecco's Medium) supplemented with 7% (v/v) dFBS (dialyzed fetal bovine serum) and hypoxanthine/thymidine (HT) via adhesion culture. A vector containing genes encoding dhfr (dihydrofolate reductase, Table 6, SEQ. ID. NO: 23) and rhBMP4 (Table 6, SEQ. ID. NO: 22) was introduced into the cultured CHO cells by using lipofectamine (lipofectamine 2000, Life technology). The vector was constructed by using pOptiVEC™-TOPO™ vector cloning kit (ThermoFisher Scientific, Catalog number: 12744017) and the gene was introduced by using lipofectamine (lipofectamine 2000, Life technology). To induce the expression of the recombinant protein rhBMP4 gene in the cells introduced with the vector comprising the gene encoding dhfr and rhBMP4 using dhfr/MTX system, the process of amplifying the productivity of the target protein rhBMP4 was repeated while increasing the concentration of MTX (1 nM-10 nM-100 nM-1 μM). Finally, the pool of viable cells in which the expression of the rhBMP4 gene was amplified at 1 μM MTX was prepared. To select clones from the prepared cell pool, cells were inoculated in a 96 well plate at the density of 0.3 cells/well, followed by culture for 10-14 days. After the culture, the cells that were grown normally were selected and the productivity of rhBMP4 of the selected clones was confirmed by ELISA.

Figure 4:
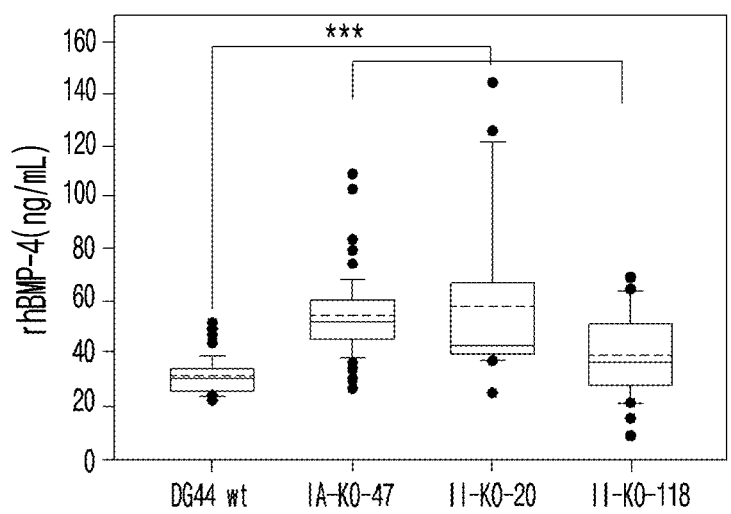
FIG. 4 is a graph illustrating the concentration of rhBMP4 produced in the BMPRIA or BMPRII gene knock-out cell line
(DG44 wt: wild type (CHO DG44 host cells);
IA-KO-47: clone 47 with BMPRIA gene knock-out;
II-KO-20: clone 20 with BMPRII gene knock-out;
II-KO-118: clone 118 with BMPRII gene knock-out).

As a result, clone #47 (IA-KO-47) selected from the BMPRIA gene knock out clones, and clones #20 and #118 (II-KO-20, II-KO-118) selected from the BMPRII gene knock clones demonstrated higher rhBMP4 productivity at average than that of the wile type clone (FIG. 4).

TABLE 6

| SEQ. ID. NO: | Protein | Amino acid sequence |
|---|---|---|
| SEQ. ID. NO: 22 | rhEMP4 | MIPGNRMLMVVLLCQVLLGGASHASLIPETGKKKVAEI QGHAGGRRSGQSHELLRDFEATLLQMFGLRRRPQPSKS AVIPDYMRDLYRLQSGEEEEEQIHSTGLEYPERPASRA NTVRSFHHEEHLENIPGTSENSAFRFLFNLSSIPENEV ISSAELRLFREQVDQGPDWERGFPHRINIYEVMKPPAEV VPGHLITRLLDTRLVHHNVTRWETFDVSPAVLRWTREK QPNYGLAIEVTHLHQTRTHQGQHVRISRSLPQGSGNWA QLRPLLVTFGHDGRGHALTRRRRAKRSPKHHSQRARKK NKNCRRHSLYVDFSDVGWNDWIVAPPGYQAFYCHGDCP FPLADHLNSTNHAIVQTLVNSVNSSIPKACCVPTELSA ISMLYLDEYDKVVLKNYQEMVVEGCGCR |
| SEQ. ID. NO: 23 | DHFR | ATGGTTCGACCATTGAACTGCATCGTCGCCGTGTCCCA AAATATGGGGATTGGCAAGAACGGAGACCTACCCTGGC CTCCGCTCAGGAACGAGTTCAAGTACTTCCAAAGAATG ACCACAACCTCTTCAGTGGAAGGTAAACAGAATCTGGT GATTATGGGTAGGAAAACCTGGTTCTCCATTCCTGAGA AGAATCGACCTTTAAAGGACAGAATTAATATAGTTCTC AGTAGAGAACTCAAAGAACCACCACGAGGAGCTCATTT TCTTGCCAAAAGTTTGGATGATGCCTTAAGACTTATTG AACAACCGGAATTGGCAAGTAAAGTAGACATGGTTTGG ATAGTCGGAGGCAGTTCTGTTTACCAGGAAGCCATGAA TCAACCAGGCCACCTCAGACTCTTTGTGACAAGGATCA TGCAGGAATTTGAAAGTGACACGTTTTTCCCAGAAATT GATTTGGGGAAATATAAACTTCTCCCAGAATACCCAGG CGTCCTCTCTGAGGTCCAGGAGGAAAAAGGCATCAAGT ATAAGTTTGAAGTCTACGAGAAGAAAGACTAA |

Experimental Example 3: Maximum Production of Target Protein in BMPRIA or BMPRII Gene Knock Out CHO Cell Line One BMPRIA gene knock out clone (IA-KO-47) and two BMPRII gene knock out clones (II-KO-20, II-KO-118) demonstrating higher target protein productivity than that of the wild type in Experimental Example 2 were selected. The three knock out clones selected above were batch-cultured by the same manner as described in Experimental Example 2 via adhesion culture. The culture medium of each cell line was collected daily and the concentration of rhBMP4 was measured by ELISA. Then, the rhBMP4 concentration at the highest productivity was compared with that of the wild type. Five clones showing high target protein productivity were selected and used as the wild type. The maximum production of the 5 wild type clones and the 3 knock out clones were averaged.

Figure 5:
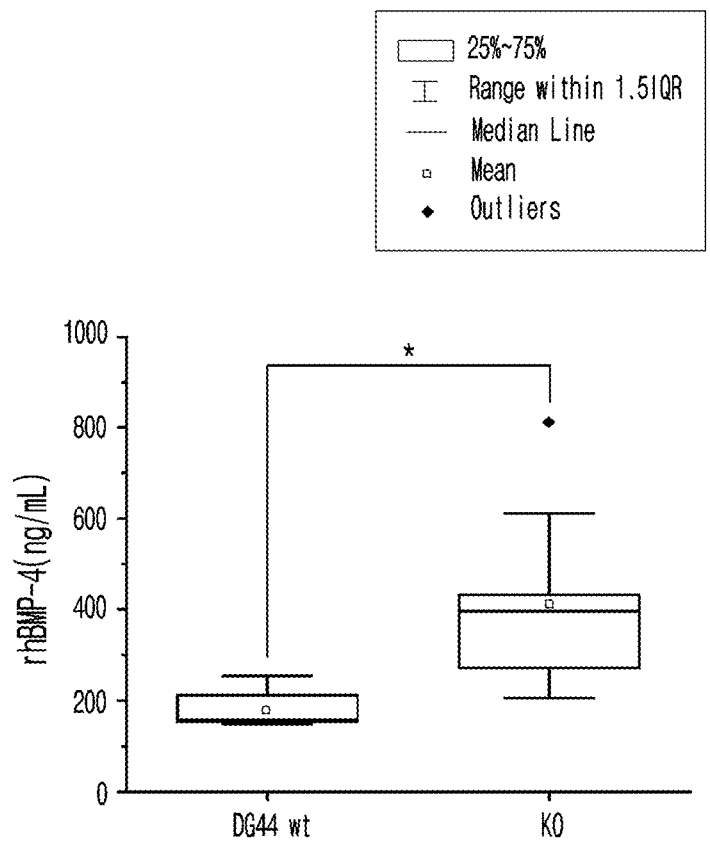
FIG. 5 is a graph illustrating the maximum production of rhBMP4 in the BMPRIA or BMPRII gene knock-out cell line
(DG44 wt: wild type (CHO DG44 host cells);
KO: IA-KO-47, II-KO-20 and II-KO-118).

As a result, it was confirmed that the maximum productivity of BMPRIA or BMPRII knock out CHO cell line (KO) was significantly higher than that of the wild type (DG44 wt) (FIG. 5).

Experimental Example 4: Target Protein Production in Suspension Culture of BMPRIA or BMPRII Gene Knock Out CHO Cell Line Protein productivity was evaluated by the same manner as described in Experimental Example 3 except that clones were suspension-cultured at this time. The culture process was as follows. First, each clone was inoculated in 30 ml of CD-OptiCHO medium (Invitrogen, Burlington, USA) supplemented with 1 μM MTX and 8 mM glutamine at the density of $5.0 \times 10^5$ cells/ml, followed by culture at 110 rpm at 37° C. From the third day after the start of the culture, fed-batch culture was performed with adding 1% (v/v) Cell Boost™ 2,5,6 supplement (HyClone) daily. During the culture, 1 ml of the medium was collected every day to measure the cell concentration, and the concentration of rhBMP4 was measured by ELISA.

Figure 6:
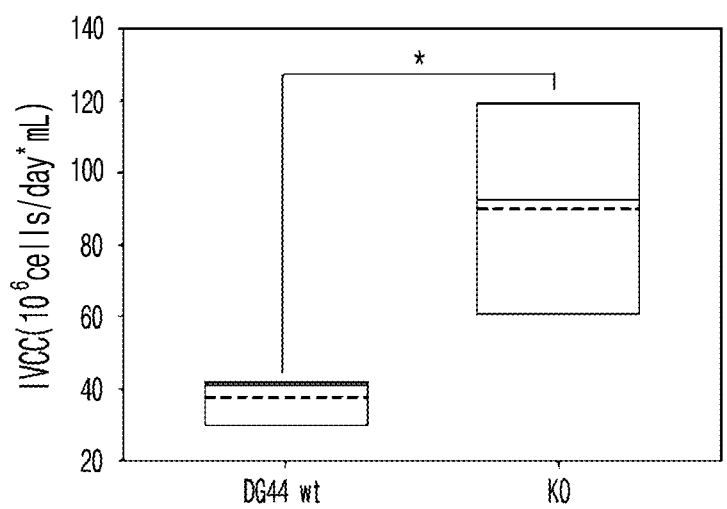
FIG. 6 is a graph illustrating the cell concentration of the BMPRIA or BMPRII gene knock-out cell line expressing recombinant human BMP4 (rhBMP4)
(DG44 wt: wild type (CHO DG44 host cells);
KO: IA-KO-47, II-KO-20 and II-KO-118).
Figure 7:
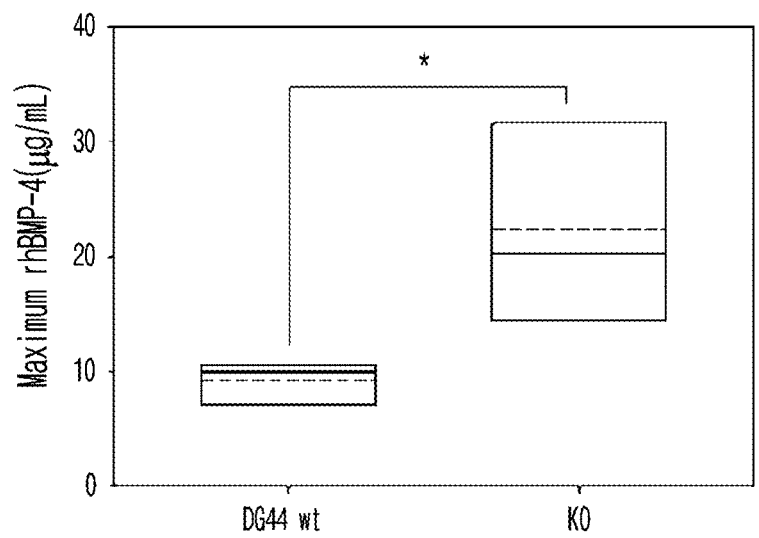
FIG. 7 is a graph illustrating the maximum production of rhBMP4 in suspension culture of the BMPRIA or BMPRII gene knock-out cell line expressing recombinant human BMP4 (rhBMP4)
(DG44 wt: wild type (CHO DG44 host cells);
KO: IA-KO-47, II-KO-20 and II-KO-118).

As a result, the accumulated cell concentration of BMPRIA or BMPRII gene knock out CHO cell line (KO) was higher than that of the wild type (DG44 wt), indicating that the signal transduction was interrupted by knocking out the BMP receptor, so that the cell growth was successfully improved (FIG. 6). As a result of the measurement of the rhBMP4 concentration, the maximum productivity of the BMPRIA or BMPRII knock out CHO cell line (KO) was remarkably higher than that of the wild type (DG44 wt) (FIG. 7).

What is claimed is:

1. A transgenic CHO cell line wherein a bone morphogenetic protein (BMP) type I receptor gene (BMPRIA) or a BMP type II receptor gene (BMPRII) is knocked out by introducing into the CHO cell line:
   a) a single vector comprising a nucleotide sequence of sgRNA represented by SEQ ID NO:6 targeting the 2nd exon nucleotide sequence of the BMPRIA gene represented by SEQ ID NO:1 and a nucleotide sequence encoding Cas9 protein represented by SEQ ID NO: 9; or
   b) a single vector comprising a nucleotide sequence of sgRNA represented by SEQ ID NO:7 targeting the 2nd exon nucleotide sequence of the BMPRII gene represented by SEQ ID NO:2, a nucleotide sequence of sgRNA represented by SEQ ID NO: 8 targeting the 5th exon nucleotide sequence of the BMPRII gene represented by SEQ ID NO:5, and a nucleotide sequence encoding Cas9 protein represented by SEQ ID NO:9.

2. The CHO cell line according to claim 1, wherein the cell line has a mutation in the $2^{nd}$ exon nucleotide sequence of the BMPRIA gene.

3. The CHO cell line according to claim 1, wherein the cell line has a mutation in the $2^{nd}$ to $5^{th}$ exon nucleotide sequences of the BMPRII gene.

4. A method for preparing a transgenic CHO cell line, wherein the BMP receptor gene BMPRIA or BMPRII is knocked-out, the method comprising the following steps:
   1) constructing a vector to knock-out the BMP receptor gene BMPRIA or BMPRII;
   2) introducing the vector of step 1) into a CHO cell line, wherein the vector is
      a) a nucleotide sequence of sgRNA represented by SEQ ID NO: 6 targeting the 2nd exon nucleotide sequence of BMPRIA gene represented by SEQ ID NO: 1 and a nucleotide sequence encoding Cas9 protein represented by SEQ ID NO: 9; or
      b) a nucleotide sequence of sgRNA represented by SEQ ID NO: 7 targeting the 2nd exon nucleotide sequence of BMPRII gene represented by SEQ ID NO: 2, a nucleotide sequence of sgRNA represented by SEQ ID NO: 8 targeting the 5th exon nucleotide sequence of BMPRII gene represented by SEQ ID NO: 5 and a nucleotide sequence encoding Cas9 protein represented by SEQ ID NO: 9; and
   3) selecting the cell line in which the BMP receptor gene BMPRIA or BMPRII has been knocked-out from those CHO cell lines introduced with the vector of step 2).

5. The method according to claim 4, wherein the vector of step 1) includes gene scissors.

6. The method according to claim 4, wherein the vector that knocks out the BMPRIA gene of step 1) is a vector comprising the nucleotide sequence of sgRNA represented by SEQ ID NO: 6 targeting the 2nd exon nucleotide sequence of BMPRIA gene represented by SEQ ID NO: 1 and a nucleotide sequence encoding Cas9 protein represented by SEQ ID NO: 9.

7. The method according to claim 4, wherein the vector that knocks out the BMPRII gene of step 1) is a vector comprising the nucleotide sequence of sgRNA represented by SEQ ID NO: 7 targeting the 2nd exon nucleotide sequence of BMPRII gene represented by SEQ ID NO: 2, a nucleotide sequence of sg RNA represented by SEQ ID NO: 8 targeting the 5th exon nucleotide sequence of BMPRII gene represented by SEQ ID NO: 5 and a nucleotide sequence encoding Cas9 protein represented by SEQ ID NO: 9.

8. A method of producing a target protein comprising the following steps:
   1) introducing a vector containing the nucleotide sequence encoding a target protein into the transgenic CHO cell line of claim 1, wherein the BMP receptor gene BMPRIA or BMPRII has been knocked-out;
   2) culturing the cell line prepared in step 1) above; and
   3) separating and purifying the target protein produced in step 2) above.

9. The method according to claim 8, wherein the CHO cell line of step 1) is a dihydrofolate reductase (DHFR) gene knock out cell line.

10. The method according to claim 8, wherein the vector of step 1) additionally includes a nucleotide sequence encoding DHFR protein.

11. The method according to claim 8, wherein the culture in step 2) is performed by treating with, methotrexate (MTX).

12. The method according to claim 8, wherein the target protein is selected from the group consisting of BMP2, BMP3, BMP4, BMP5, BM P6, BMP7, BMP8, BMP9, BMP10, BMP11, BMP12, BMP13, BMP14 and BMP15.

13. The transgenic CHO cell line of claim 1, wherein the vector comprising the nucleotide sequence of sgRNA targeting the 2nd exon nucleotide sequence of the BMPRIA gene comprises the nucleotide sequence represented by SEQ ID NO:10.

14. The transgenic CHO cell line of claim 1, wherein the vector comprising the nucleotide sequence of sg RNA targeting the 2nd exon nucleotide sequence of the BMPRII gene comprises the nucleotide sequence represented by SEQ ID NO:11.

15. The transgenic CHO cell line of claim 1, wherein the vector comprising the nucleotide sequence of sg RNA targeting the 5th exon nucleotide sequence of the BMPRII gene comprises the nucleotide sequence represented by SEQ ID NO:12.

16. The transgenic CHO cell line of claim 1, wherein the vector comprising the nucleotide sequence encoding the Cas9 protein comprises the nucleotide sequence represented by SEQ ID NO:13.

* * * * *

SEQUENCE LISTING

<160> NUMBER OF SEQ ID NOS: 35

<210> SEQ ID NO 1
<211> LENGTH: 163
<212> TYPE: DNA
<213> ORGANISM: Artificial Sequence
<220> FEATURE:
<223> OTHER INFORMATION: BMPRIA gene exon2

<400> SEQUENCE: 1

```
atgcatgtgt tattaatagc atcatctggg cagtggcctg agcagtaaca ctttaagaaa      60
ggcaaagtat cctccggggc taaagtcact ccattttctg gcttcttctg gtccaagtct     120
gatttcatac cagtaccatg gagcatactg tctagattct gcc                       163
```

<210> SEQ ID NO 2
<211> LENGTH: 171
<212> TYPE: DNA
<213> ORGANISM: Artificial Sequence
<220> FEATURE:
<223> OTHER INFORMATION: BMPRII gene exon2

<400> SEQUENCE: 2

```
cttcccagaa tcaagaacgg ctgtgtgcat ttaaagatcc ctaccagcaa gaccttggga      60
taggtgagag tagaatctct catgaaaatg ggacaatatt atgctccaaa ggtagcacat     120
gctatggtct atgggagaaa tcaaaagggg acatcaatct tgtgaaacaa g              171
```

<210> SEQ ID NO 3
<211> LENGTH: 171
<212> TYPE: DNA
<213> ORGANISM: Artificial Sequence
<220> FEATURE:
<223> OTHER INFORMATION: BMPRII gene exon3

<400> SEQUENCE: 3

```
gatgttggtc tcacattggc gatcctcaag agtgtcacta tgaagaatgt gtagtaacta      60
ctaccccacc ctcaattcag aatggaacat accgtttttg ctgctgtagt acagatttat     120
gtaatgtcaa ctttactgag aattttccac ctcctgatac aacaccactc a              171
```

<210> SEQ ID NO 4
<211> LENGTH: 111
<212> TYPE: DNA

```
<213> ORGANISM: Artificial Sequence
<220> FEATURE:
<223> OTHER INFORMATION: BMPRII gene exon4

<400> SEQUENCE: 4
gtccacctca ttcatttaat cgagatgaga caataatcat tgctttggca tcagtctctg    60
tattagctgt tttgatagtc gccttatgtt ttggatacag aatgttgaca g            111

<210> SEQ ID NO 5
<211> LENGTH: 92
<212> TYPE: DNA
<213> ORGANISM: Artificial Sequence
<220> FEATURE:
<223> OTHER INFORMATION: BMPRII gene exon5

<400> SEQUENCE: 5
gagaccgaaa acaaggcctt cacagtatga acatgatgga agcagcggcg tcagagcctt    60
ctctggactt ggataatctg aagctgctgg ag                                  92

<210> SEQ ID NO 6
<211> LENGTH: 23
<212> TYPE: DNA
<213> ORGANISM: Artificial Sequence
<220> FEATURE:
<223> OTHER INFORMATION: sgRNA for BMPRIA gene exon2

<400> SEQUENCE: 6
gaaaggcaaa gtatcctccg ggg                                            23

<210> SEQ ID NO 7
<211> LENGTH: 23
<212> TYPE: DNA
<213> ORGANISM: Artificial Sequence
<220> FEATURE:
<223> OTHER INFORMATION: sgRNA for BMPRII gene exon2

<400> SEQUENCE: 7
gggacaatat tatgctccaa agg                                            23

<210> SEQ ID NO 8
<211> LENGTH: 23
<212> TYPE: DNA
<213> ORGANISM: Artificial Sequence
<220> FEATURE:
<223> OTHER INFORMATION: sgRNA for BMPRII gene exon5

<400> SEQUENCE: 8
agcggcgtca gagccttctc tgg                                            23

<210> SEQ ID NO 9
<211> LENGTH: 1368
<212> TYPE: PRT
<213> ORGANISM: Artificial Sequence
<220> FEATURE:
<223> OTHER INFORMATION: Cas protein

<400> SEQUENCE: 9
```

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

-continued

Gly Ala Leu Leu Phe Asp Ser Gly Glu Thr Ala Glu Ala Thr Arg Leu
 50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu

```
            465                 470                 475                 480
    Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                    500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Glu Gln
                    530                 535                 540

Lys Lys Ala Ile Val Asp Leu Leu Phe Lys Thr Asn Arg Lys Val Thr
    545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                    580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                    610                 615                 620

Leu Phe Glu Asp Arg Glu Met Ile Glu Glu Arg Leu Lys Thr Tyr Ala
    625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                    660                 665                 670

Lys Gln Ser Gly Lys Thr Ile Leu Asp Phe Leu Lys Ser Asp Gly Phe
                    675                 680                 685

Ala Asn Arg Asn Phe Met Gln Leu Ile His Asp Asp Ser Leu Thr Phe
                    690                 695                 700

Lys Glu Asp Ile Gln Lys Ala Gln Val Ser Gly Gln Gly Asp Ser Leu
    705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                    740                 745                 750

Arg His Lys Pro Glu Asn Ile Val Ile Glu Met Ala Arg Glu Asn Gln
                    755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
    785                 790                 795                 800

Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                    820                 825                 830

Leu Ser Asp Tyr Asp Val Asp His Ile Val Pro Gln Ser Phe Leu Lys
                    835                 840                 845

Asp Asp Ser Ile Asp Asn Lys Val Leu Thr Arg Ser Asp Lys Asn Arg
                    850                 855                 860

Gly Lys Ser Asp Asn Val Pro Ser Glu Glu Val Val Lys Lys Met Lys
    865                 870                 875                 880

Asn Tyr Trp Arg Gln Leu Leu Asn Ala Lys Leu Ile Thr Gln Arg Lys
                    885                 890                 895
```

```
Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
            1045                1050                1055

Ile Arg Lys Arg Pro Leu Ile Glu Thr Asn Gly Glu Thr Gly Glu Ile
            1060                1065                1070

Val Trp Asp Lys Gly Arg Asp Phe Ala Thr Val Arg Lys Val Leu Ser
            1075                1080                1085

Met Pro Gln Val Asn Ile Val Lys Lys Thr Glu Val Gln Thr Gly Gly
            1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
            1125                1130                1135

Pro Thr Val Ala Tyr Ser Val Leu Val Val Ala Lys Val Glu Lys Gly
            1140                1145                1150

Lys Ser Lys Lys Leu Lys Ser Val Lys Glu Leu Leu Gly Ile Thr Ile
            1155                1160                1165

Met Glu Arg Ser Ser Phe Glu Lys Asn Pro Ile Asp Phe Leu Glu Ala
            1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
            1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
            1285                1290                1295

His Arg Asp Lys Pro Ile Arg Glu Gln Ala Glu Asn Ile Ile His Leu
            1300                1305                1310
```

Phe Thr Leu Thr Asn Leu Gly Ala Pro Ala Ala Phe Lys Tyr Phe Asp
    1315                1320                1325

Thr Thr Ile Asp Arg Lys Arg Tyr Thr Ser Thr Lys Glu Val Leu Asp
    1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp
            1365

<210> SEQ ID NO 10
<211> LENGTH: 2492
<212> TYPE: DNA
<213> ORGANISM: Artificial Sequence
<220> FEATURE:
<223> OTHER INFORMATION: sgRNA expression vector for BMPRIA gene exon2

<400> SEQUENCE: 10

| | | |
|---|---|---|
| gacgaagact caattgtcga ttagtgaacg gatctcgacg gtatcgatca cgagactagc | 60 |
| ctcgagcggc cgccccttc accgagggcc tatttcccat gattccttca tatttgcata | 120 |
| tacgatacaa ggctgttaga gagataattg aattaatttt gactgtaaac acaaagatat | 180 |
| tagtacaaaa tacgtgacgt agaaagtaat aatttcttgg gtagtttgca gttttaaaat | 240 |
| tatgttttaa aatggactat catatgctta ccgtaacttg aaagtatttc gatttcttgg | 300 |
| ctttatatat cttgtggaaa ggacgaaaca ccggaaaggc aaagtatcct ccggggtttt | 360 |
| tagagctaga aatagcaagt taaaataagg ctagtccgtt atcaacttga aaaagtggca | 420 |
| ccgagtcggt gctttttct agattcgcga tgtacgggcc agatatacgc gttgacattg | 480 |
| attattgact agttgtcttc ctgcattaat gaatcggcca acgcgcgggg agaggcggtt | 540 |
| tgcgtattgg gcgctcttcc gcttcctcgc tcactgactc gctgcgctcg gtcgttcggc | 600 |
| tgcggcgagc ggtatcagct cactcaaagg cggtaatacg gttatccaca gaatcagggg | 660 |
| ataacgcagg aaagaacatg tgagcaaaag gccagcaaaa ggccaggaac cgtaaaaagg | 720 |
| ccgcgttgct ggcgtttttc cataggctcc gcccccctga cgagcatcac aaaaatcgac | 780 |
| gctcaagtca gaggtggcga aacccgacag gactataaag ataccaggcg tttccccctg | 840 |
| gaagctccct cgtgcgctct cctgttccga ccctgccgct taccggatac ctgtccgcct | 900 |
| ttctcccttc gggaagcgtg gcgctttctc aatgctcacg ctgtaggtat ctcagttcgg | 960 |
| tgtaggtcgt tcgctccaag ctgggctgtg tgcacgaacc ccccgttcag cccgaccgct | 1020 |
| gcgccttatc cggtaactat cgtcttgagt ccaacccggt aagacacgac ttatcgccac | 1080 |
| tggcagcagc cactggtaac aggattagca gagcgaggta tgtaggcggt gctacagagt | 1140 |
| tcttgaagtg gtggcctaac tacggctaca ctagaaggac agtatttggt atctgcgctc | 1200 |
| tgctgaagcc agttaccttc ggaaaaagag ttggtagctc ttgatccggc aaacaaacca | 1260 |
| ccgctggtag cggtggtttt tttgtttgca agcagcagat tacgcgcaga aaaaaggat | 1320 |
| ctcaagaaga tcctttgatc ttttctacgg ggtctgacgc tcagtggaac gaaaactcac | 1380 |
| gttaagggat tttggtcatg agattatcaa aaaggatctt cacctagatc cttttaaatt | 1440 |
| aaaaatgaag ttttaaatca atctaaagta tatatgagta aacttggtct gacagttacc | 1500 |
| aatgcttaat cagtgaggca cctatctcag cgatctgtct atttcgttca tccatagttg | 1560 |
| cctgactccc cgtcgtgtag ataactacga tacgggaggg cttaccatct ggccccagtg | 1620 |
| ctgcaatgat accgcgagat ccacgctcac cggctccaga tttatcagca ataaccagc | 1680 |
| cagccggaag ggccgagcgc agaagtggtc ctgcaacttt atccgcctcc atccagtcta | 1740 |

```
ttaattgttg ccgggaagct agagtaagta gttcgccagt taatagtttg cgcaacgttg    1800
ttgccattgc tacaggcatc gtggtgtcac gctcgtcgtt tggtatggct tcattcagct    1860
ccggttccca acgatcaagg cgagttacat gatcccccat gttgtgcaaa aaagcggtta    1920
gctccttcgg tcctccgatc gttgtcagaa gtaagttggc cgcagtgtta tcactcatgg    1980
ttatggcagc actgcataat tctcttactg tcatgccatc cgtaagatgc ttttctgtga    2040
ctggtgagta ctcaaccaag tcattctgag aatagtgtat cgggcgaccg agttgctctt    2100
gcccggcgtc aatacgggat aataccgcgc cacatagcag aactttaaaa gtgctcatca    2160
ttggaaaacg ttcttcgggg cgaaaactct caaggatctt accgctgttg agatccagtt    2220
cgatgtaacc cactcgtgca cccaactgat cttcagcatc ttttactttc accagcgttt    2280
ctgggtgagc aaaaacagga aggcaaaatg ccgcaaaaaa gggaataagg gcgacacgga    2340
aatgttgaat actcatactc ttcctttttc aatattattg aagcatttat cagggttatt    2400
gtctcatgag cggatacata tttgaatgta tttagaaaaa taaacaaata ggggttccgc    2460
gcacatttcc ccgaaaagtg ccacctgacg tc                                  2492

<210> SEQ ID NO 11
<211> LENGTH: 2492
<212> TYPE: DNA
<213> ORGANISM: Artificial Sequence
<220> FEATURE:
<223> OTHER INFORMATION: sgRNA expression vector for BMPRII gene exon2

<400> SEQUENCE: 11
gacgaagact caattgtcga ttagtgaacg gatctcgacg gtatcgatca cgagactagc      60
ctcgagcggc cgcccccttc accgagggcc tatttcccat gattccttca tatttgcata    120
tacgatacaa ggctgttaga gagataattg gaattaattt gactgtaaac acaaagatat    180
tagtacaaaa tacgtgacgt agaaagtaat aatttcttgg gtagtttgca gttttaaaat    240
tatgttttaa aatggactat catatgctta ccgtaacttg aaagtatttc gatttcttgg    300
ctttatatat cttgtggaaa ggacgaaaca ccggggacaa tattatgctc aaagggttt     360 tagagctaga aatagcaagt taaaataagg ctagtccgtt atcaacttga aaaagtggca    420
ccgagtcggt gcttttttct agattcgcga tgtacgggcc agatatacgc gttgacattg    480
attattgact agttgtcttc ctgcattaat gaatcggcca acgcgcgggg agaggcggtt    540
tgcgtattgg gcgctcttcc gcttcctcgc tcactgactc gctgcgctcg gtcgttcggc    600
tgcggcgagc ggtatcagct cactcaaagg cggtaatacg gttatccaca gaatcagggg    660
ataacgcagg aaagaacatg tgagcaaaag gccagcaaaa ggccaggaac cgtaaaaagg    720
ccgcgttgct ggcgtttttc cataggctcc gcccccctga cgagcatcac aaaaatcgac    780
gctcaagtca gaggtggcga aacccgacag gactataaag ataccaggcg tttccccctg    840
gaagctccct cgtgcgctct cctgttccga ccctgccgct taccggatac ctgtccgcct    900
ttctcccttc gggaagcgtg gcgctttctc aatgctcacg ctgtaggtat ctcagttcgg    960
tgtaggtcgt tcgctccaag ctgggctgtg tgcacgaacc ccccgttcag cccgaccgct   1020
gcgccttatc cggtaactat cgtcttgagt ccaacccggt aagacacgac ttatcgccac   1080
tggcagcagc cactggtaac aggattagca gagcgaggta tgtaggcggt gctacagagt   1140
tcttgaagtg gtggcctaac tacggctaca ctagaaggac agtatttggt atctgcgctc   1200
tgctgaagcc agttaccttc ggaaaaagag ttggtagctc ttgatccggc aaacaaacca   1260
```

```
ccgctggtag cggtggtttt tttgtttgca agcagcagat tacgcgcaga aaaaaaggat    1320
ctcaagaaga tcctttgatc ttttctacgg ggtctgacgc tcagtggaac gaaaactcac    1380
gttaagggat tttggtcatg agattatcaa aaaggatctt cacctagatc cttttaaatt    1440
aaaaatgaag ttttaaatca atctaaagta tatatgagta aacttggtct gacagttacc    1500
aatgcttaat cagtgaggca cctatctcag cgatctgtct atttcgttca tccatagttg    1560
cctgactccc cgtcgtgtag ataactacga tacgggaggg cttaccatct ggccccagtg    1620
ctgcaatgat accgcgagat ccacgctcac cggctccaga tttatcagca ataaaccagc    1680
cagccggaag ggccgagcgc agaagtggtc ctgcaacttt atccgcctcc atccagtcta    1740
ttaattgttg ccgggaagct agagtaagta gttcgccagt taatagtttg cgcaacgttg    1800
ttgccattgc tacaggcatc gtggtgtcac gctcgtcgtt tggtatggct tcattcagct    1860
ccggttccca acgatcaagg cgagttacat gatcccccat gttgtgcaaa aaagcggtta    1920
gctccttcgg tcctccgatc gttgtcagaa gtaagttggc cgcagtgtta tcactcatgg    1980
ttatggcagc actgcataat tctcttactg tcatgccatc cgtaagatgc ttttctgtga    2040
ctggtgagta ctcaaccaag tcattctgag aatagtgtat gcggcgaccg agttgctctt    2100
gcccggcgtc aatacgggat aataccgcgc cacatagcag aactttaaaa gtgctcatca    2160
ttggaaaacg ttcttcgggg cgaaaactct caaggatctt accgctgttg agatccagtt    2220
cgatgtaacc cactcgtgca cccaactgat cttcagcatc ttttactttc accagcgttt    2280
ctgggtgagc aaaaacagga aggcaaaatg ccgcaaaaaa gggaataagg gcgacacgga    2340
aatgttgaat actcatactc ttcctttttc aatattattg aagcatttat cagggttatt    2400
gtctcatgag cggatacata tttgaatgta tttagaaaaa taaacaaata ggggttccgc    2460
gcacatttcc ccgaaaagtg ccacctgacg tc                                  2492

<210> SEQ ID NO 12
<211> LENGTH: 2492
<212> TYPE: DNA
<213> ORGANISM: Artificial Sequence
<220> FEATURE:
<223> OTHER INFORMATION: sgRNA expression vector for BMPRII gene exon5

<400> SEQUENCE: 12
gacgaagact caattgtcga ttagtgaacg gatctcgacg gtatcgatca cgagactagc      60
ctcgagcggc cgccccctc accgagggcc tatttcccat gattccttca tatttgcata    120
tacgatacaa ggctgttaga gagataattg gaattaattt gactgtaaac acaaagatat    180
tagtacaaaa tacgtgacgt agaaagtaat aatttcttgg gtagtttgca gttttaaaat    240
tatgttttaa aatggactat catatgctta ccgtaacttg aaagtatttc gatttcttgg    300
ctttatatat cttgtggaaa ggacgaaaca ccgagcggcg tcagagcctt ctctgggttt    360
tagagctaga aatagcaagt taaaataagg ctagtccgtt atcaacttga aaaagtggca    420
ccgagtcggt gcttttttct agattcgcga tgtacgggcc agatatacgc gttgacattg    480
attattgact agttgtcttc ctgcattaat gaatcggcca acgcgcgggg agaggcggtt    540
tgcgtattgg gcgctcttcc gcttcctcgc tcactgactc gctgcgctcg tcgttcggc    600 tgcggcgagc ggtatcagct cactcaaagg cggtaatacg gttatccaca gaatcagggg    660
ataacgcagg aaagaacatg tgagcaaaag gccagcaaaa ggccaggaac cgtaaaaagg    720
ccgcgttgct ggcgtttttc cataggctcc gcccccctga cgagcatcac aaaaatcgac    780
gctcaagtca gaggtggcga aacccgacag gactataaag ataccaggcg tttccccctg    840
```

```
gaagctccct cgtgcgctct cctgttccga ccctgccgct taccggatac ctgtccgcct    900 ttctccttc gggaagcgtg gcgctttctc aatgctcacg ctgtaggtat ctcagttcgg    960
tgtaggtcgt tcgctccaag ctgggctgtg tgcacgaacc ccccgttcag cccgaccgct   1020
gcgccttatc cggtaactat cgtcttgagt ccaacccggt aagacacgac ttatcgccac   1080
tggcagcagc cactggtaac aggattagca gagcgaggta tgtaggcggt gctacagagt   1140
tcttgaagtg gtggcctaac tacgctaca ctagaaggac agtatttggt atctgcgctc    1200
tgctgaagcc agttaccttc ggaaaaagag ttggtagctc ttgatccggc aaacaaacca   1260
ccgctggtag cggtggtttt tttgtttgca agcagcagat tacgcgcaga aaaaaggat    1320 ctcaagaaga tcctttgatc ttttctacgg ggtctgacgc tcagtggaac gaaaactcac   1380
gttaagggat tttggtcatg agattatcaa aaaggatctt cacctagatc cttttaaatt   1440
aaaaatgaag ttttaaatca atctaaagta tatatgagta aacttggtct gacagttacc   1500
aatgcttaat cagtgaggca cctatctcag cgatctgtct atttcgttca tccatagttg   1560
cctgactccc cgtcgtgtag ataactacga tacgggaggg cttaccatct ggccccagtg   1620
ctgcaatgat accgcgagat ccacgctcac cggctccaga tttatcagca ataaaccagc   1680
cagccggaag ggccgagcgc agaagtggtc ctgcaacttt atccgcctcc atccagtcta   1740
ttaattgttg ccgggaagct agagtaagta gttcgccagt taatagtttg cgcaacgttg   1800
ttgccattgc tacaggcatc gtggtgtcac gctcgtcgtt tggtatggct tcattcagct   1860
ccggttccca acgatcaagg cgagttacat gatccccat gttgtgcaaa aaagcggtta    1920
gctccttcgg tcctccgatc gttgtcagaa gtaagttggc cgcagtgtta tcactcatgg   1980
ttatggcagc actgcataat tctcttactg tcatgccatc cgtaagatgc ttttctgtga   2040
ctggtgagta ctcaaccaag tcattctgag aatagtgtat gcggcgaccg agttgctctt   2100
gcccggcgtc aatacgggat aataccgcgc cacatagcag aactttaaaa gtgctcatca   2160
ttggaaaacg ttcttcgggg cgaaaactct caaggatctt accgctgttg agatccagtt   2220
cgatgtaacc cactcgtgca cccaactgat cttcagcatc ttttactttc accagcgttt   2280
ctgggtgagc aaaaacagga aggcaaaatg ccgcaaaaaa gggaataagg gcgacacgga   2340
aatgttgaat actcatactc ttcctttttc aatattattg aagcatttat cagggttatt   2400
gtctcatgag cggatacata tttgaatgta tttagaaaaa taaacaaata ggggttccgc   2460
gcacatttcc ccgaaaagtg ccacctgacg tc                                 2492
```

<210> SEQ ID NO 13
<211> LENGTH: 7383
<212> TYPE: DNA
<213> ORGANISM: Artificial Sequence
<220> FEATURE:
<223> OTHER INFORMATION: Cas protein expression vector

<400> SEQUENCE: 13

```
gacggatcgg gagatctccc gatccccat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
```

```
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgccacc    900
atggacaaga agtacagcat cggcctggac atcggtacca cagcgtgggc tgggccgtg     960 atcaccgacg agtacaaggt gcccagcaag aagttcaagg tgctgggcaa caccgaccgc   1020
cacagcatca agaagaacct gatcggcgcc ctgctgttcg acagcggcga gaccgccgag   1080
gccacccgcc tgaagcgcac cgcccgccgc cgctacaccc gccgcaagaa ccgcatctgc   1140
tacctgcagg agatcttcag caacgagatg gccaaggtgg acgacagctt cttccaccgc   1200
ctggaggaga gcttcctggt ggaggaggac aagaagcacg agcgccaccc catcttcggc   1260
aacatcgtgg acgaggtggc ctaccacgag aagtacccca ccatctacca cctgcgcaag   1320
aagctggtgg acagcaccga caaggccgac ctgcgcctga tctacctggc cctggcccac   1380
atgatcaagt tccgcggcca cttcctgatc gagggcgacc tgaaccccga caacagcgac   1440
gtggacaagc tgttcatcca gctggtgcag acctacaacc agctgttcga ggagaacccc   1500
atcaacgcca gcggcgtgga cgccaaggcc atcctgagcg cccgcctgag caagagccgc   1560
cgcctggaga acctgatcgc ccagctgccc ggcgagaaga gaacggcct gttcggcaac   1620 ctgatcgccc tgagcctggg cctgacccc aacttcaaga gcaacttcga cctggccgag   1680
gacgccaagc tgcagctgag caaggacacc tacgacgacg acctggacaa cctgctggcc   1740
cagatcggcg accagtacgc cgacctgttc ctggccgcca agaacctgag cgacgccatc   1800
ctgctgagcg acatcctgcg cgtgaacacc gagatcacca aggcccccct gagcgccagc   1860
atgatcaagc gctacgacga gcaccaccag gacctgaccc tgctgaaggc cctggtgcgc   1920
cagcagctgc ccgagaagta caaggagatc ttcttcgacc agagcaagaa cggctacgcc   1980
ggctacatcg acggcggcgc cagccaggag gagttctaca agttcatcaa gcccatcctg   2040
gagaagatgg acggcaccga ggagctgctg gtgaagctga accgcgagga cctgctgcgc   2100
aagcagcgca ccttcgacaa cggcagcatc cccaccagat ccacctgggg cgagctgcac   2160
gccatcctgc gccgcagga ggacttctac cccttcctga aggacaaccg cgagaagatc   2220
gagaagatcc tgaccttccg catcccctac tacgtgggcc ccctggcccg cggcaacagc   2280
cgcttcgcct ggatgacccg caagagcgag gagaccatca ccccctgaa cttcgaggag   2340 gtggtggaca agggcgccag cgcccagagc ttcatcgagc gcatgaccaa cttcgacaag   2400
aacctgccca acgagaaggt gctgcccaag cacagcctgc tgtacgagta cttcaccgtg   2460
tacaacgagc tgaccaaggt gaagtacgtg accgagggca tgcgcaagcc cgccttcctg   2520
agcggcgagc agaagaaggc catcgtggac ctgctgttca gaccaaccg caaggtgacc   2580 gtgaagcagc tgaaggagga ctacttcaag aagatcgagt gcttcgacag cgtggagatc   2640
agcggcgtgg aggaccgctt caacgccagc ctgggcacct accacgacct gctgaagatc   2700
atcaaggaca aggacttcct ggacaacgag gagaacgagg acatcctgga ggacatcgtg   2760
```

```
ctgaccctga ccctgttcga ggaccgcgag atgatcgagg agcgcctgaa gacctacgcc   2820
cacctgttcg acgacaaggt gatgaagcag ctgaagcgcc gccgctacac cggctggggc   2880
cgcctgagcc gcaagcttat caacggcatc cgcgacaagc agagcggcaa gaccatcctg   2940
gacttcctga gagcgacgg cttcgccaac cgcaacttca tgcagctgat ccacgacgac   3000
agcctgacct tcaaggagga catccagaag gcccaggtga gcggccaggg cgacagcctg   3060
cacgagcaca tcgccaacct ggccggcagc cccgccatca gaagggcat cctgcagacc    3120 gtgaaggtgg tggacgagct ggtgaaggtg atgggccgcc acaagcccga gaacatcgtg   3180
atcgagatgg cccgcgagaa ccagaccacc cagaagggcc agaagaacag ccgcgagcgc   3240
atgaagcgca tcgaggaggg catcaaggag ctgggcagcc agatcctgaa ggagcacccc   3300
gtggagaaca cccagctgca gaacgagaag ctgtacctgt actacctgca gaacggccgc   3360
gacatgtacg tggaccagga gctggacatc aaccgcctga gcgactacga cgtggaccac   3420
atcgtgcccc agagcttcct gaaggacgac agcatcgaca caaggtgct gacccgcagc    3480 gacaagaacc gcggcaagag cgacaacgtg cccagcgagg aggtggtgaa gaagatgaag   3540
aactactggc gccagctgct gaacgccaag ctgatcaccc agcgcaagtt cgacaacctg   3600
accaaggccg agcgcggcgg cctgagcgag ctggacaagg ccggcttcat caagcgccag   3660
ctggtggaga cccgccagat caccaagcac gtggcccaga tcctggacag ccgcatgaac   3720
accaagtacg acgagaacga caagctgatc cgcgaggtga aggtgatcac cctgaagagc   3780
aagctggtga cgacttccg caaggacttc cagttctaca aggtgcgcga gatcaacaac   3840
taccaccacg cccacgacgc ctacctgaac gccgtggtgg gcaccgccct gatcaagaag   3900
taccccaagc tggagagcga gttcgtgtac ggcgactaca aggtgtacga cgtgcgcaag   3960
atgatcgcca agagcgagca ggagatcggc aaggccaccg ccaagtactt cttctacagc   4020
aacatcatga acttcttcaa gaccgagatc accctggcca acggcgagat ccgcaagcgc   4080
cccctgatcg agaccaacgg cgagaccggc gagatcgtgt gggacaaggg ccgcgacttc   4140
gccaccgtgc gcaaggtgct gagcatgccc caggtgaaca tcgtgaagaa gaccgaggtg   4200
cagaccggcg gcttcagcaa ggagagcatc ctgcccaagc gcaacagcga caagctgatc   4260
gcccgcaaga aggactggga ccccaagaag tacggcggct tcgacagccc caccgtggcc   4320
tacagcgtgc tggtggtggc caaggtggag aagggcaaga gcaagaagct gaagagcgtg   4380
aaggagctgc tgggcatcac catcatggag cgcagcagct tcgagaagaa ccccatcgac   4440
ttcctggagg ccaagggcta caaggaggtg aagaaggacc tgatcatcaa gctgcccaag   4500
tacagcctgt tcgagctgga aacggccgc aagcgcatgc tggccagcgc cggcgagctg   4560
cagaagggca cgagctggc cctgcccagc aagtacgtga acttcctgta cctggccagc   4620
cactacgaga agctgaaggg cagccccgag gacaacgagc agaagcagct gttcgtggag   4680
cagcacaagc actacctgga cgagatcatc gagcagatca gcgagttcag caagcgcgtg   4740
atcctggccg acgccaacct ggacaaggtg ctgagcgcct acaacaagca ccgcgacaag   4800
cccatccgcg agcaggccga gaacatcatc cacctgttca ccctgaccaa cctgggcgcc   4860
cccgccgcct tcaagtactt cgacaccacc atcgaccgca gcgctacac cagcaccaag   4920 gaggtgctgg acgccaccct gatccaccag agcatcaccg tctgtacga cccgcatc     4980 gacctgagcc agctgggcgg cgacggcggc tccggacctc caaagaaaaa gagaaaagta   5040 taccctacg acgtgcccga ctacgcctaa taactcgagc atgcatctag agggccctat    5100
```

```
tctatagtgt cacctaaatg ctagagctcg ctgatcagcc tcgactgtgc cttctagttg    5160
ccagccatct gttgtttgcc cctccccgt gccttccttg accctggaag gtgccactcc    5220
cactgtcctt tcctaataaa atgaggaaat tgcatcgcat tgtctgagta ggtgtcattc    5280
tattctgggg ggtggggtgg ggcaggacag caaggggag gattgggaag acaatagcag     5340
gcatgctggg gatgcggtgg gctctatggc ttctgaggcg gaaagaacca gctgcattaa    5400
tgaatcggcc aacgcgcggg gagaggcggt ttgcgtattg ggcgctcttc cgcttcctcg    5460
ctcactgact cgctgcgctc ggtcgttcgg ctgcggcgag cggtatcagc tcactcaaag    5520
gcggtaatac ggttatccac agaatcaggg gataacgcag gaaagaacat gtgagcaaaa    5580
ggccagcaaa aggccaggaa ccgtaaaaag gccgcgttgc tggcgttttt ccataggctc    5640
cgcccccctg acgagcatca aaaaatcga cgctcaagtc agaggtggcg aaacccgaca    5700
ggactataaa gataccaggc gtttccccct ggaagctccc tcgtgcgctc tcctgttccg    5760
accctgccgc ttaccggata cctgtccgcc tttctccctt cgggaagcgt ggcgctttct    5820
caatgctcac gctgtaggta tctcagttcg gtgtaggtcg ttcgctccaa gctgggctgt    5880
gtgcacgaac cccccgttca gcccgaccgc tgcgccttat ccggtaacta tcgtcttgag    5940
tccaacccgg taagacacga cttatcgcca ctggcagcag ccactggtaa caggattagc    6000
agagcgaggt atgtaggcgg tgctacagag ttcttgaagt ggtggcctaa ctacggctac    6060
actagaagga cagtatttgg tatctgcgct ctgctgaagc cagttacctt cggaaaaaga    6120
gttggtagct cttgatccgg caaacaaacc accgctggta gcggtggttt ttttgtttgc    6180
aagcagcaga ttacgcgcag aaaaaaagga tctcaagaag atcctttgat cttttctacg    6240
gggtctgacg ctcagtggaa cgaaaactca cgttaaggga ttttggtcat gagattatca    6300
aaaaggatct tcacctagat ccttttaaat taaaaatgaa gttttaaatc aatctaaagt    6360
atatatgagt aaacttggtc tgacagttac caatgcttaa tcagtgaggc acctatctca    6420
gcgatctgtc tatttcgttc atccatagtt gcctgactcc ccgtcgtgta gataactacg    6480
atacgggagg gcttaccatc tggccccagt gctgcaatga taccgcgaga cccacgctca    6540
ccggctccag atttatcagc aataaaccag ccagccggaa gggccgagcg cagaagtggt    6600
cctgcaactt tatccgcctc catccagtct attaattgtt gccgggaagc tagagtaagt    6660
agttcgccag ttaatagttt gcgcaacgtt gttgccattg ctacaggcat cgtggtgtca    6720
cgctcgtcgt ttggtatggc ttcattcagc tccggttccc aacgatcaag gcgagttaca    6780
tgatccccca tgttgtgcaa aaaagcggtt agctccttcg gtcctccgat cgttgtcaga    6840
agtaagttgg ccgcagtgtt atcactcatg gttatggcag cactgcataa ttctcttact    6900
gtcatgccat ccgtaagatg cttttctgtg actggtgagt actcaaccaa gtcattctga    6960
gaatagtgta tgcggcgacc gagttgctct tgcccggcgt caatacggga taataccgcg    7020
ccacatagca gaactttaaa agtgctcatc attggaaaac gttcttcggg gcgaaaactc    7080
tcaaggatct taccgctgtt gagatccagt tcgatgtaac ccactcgtgc acccaactga    7140
tcttcagcat cttttacttt caccagcgtt tctgggtgag caaaaacagg aaggcaaaat    7200
gccgcaaaaa agggaataag ggcgacacgg aaatgttgaa tactcatact cttcctttt     7260
caatattatt gaagcattta tcagggttat tgtctcatga gcggatacat atttgaatgt    7320
atttagaaaa ataaacaaat aggggttccg cgcacatttc cccgaaaagt gccacctgac    7380
gtc                                                                  7383
```

<210> SEQ ID NO 14
<211> LENGTH: 22
<212> TYPE: DNA
<213> ORGANISM: Artificial Sequence
<220> FEATURE:
<223> OTHER INFORMATION: BMPRIA gene exon2 Forward primer

<400> SEQUENCE: 14
ggaactcact ctgtagaaga gg                                              22

<210> SEQ ID NO 15
<211> LENGTH: 21
<212> TYPE: DNA
<213> ORGANISM: Artificial Sequence
<220> FEATURE:
<223> OTHER INFORMATION: BMPRIA gene exon2 Reverse primer

<400> SEQUENCE: 15
gtgttggggc accctttgat c                                               21

<210> SEQ ID NO 16
<211> LENGTH: 20
<212> TYPE: DNA
<213> ORGANISM: Artificial Sequence
<220> FEATURE:
<223> OTHER INFORMATION: BMPRII gene exon2-3 Forward primer

<400> SEQUENCE: 16
agaacggctg tgtgcattta                                                 20

<210> SEQ ID NO 17
<211> LENGTH: 21
<212> TYPE: DNA
<213> ORGANISM: Artificial Sequence
<220> FEATURE:
<223> OTHER INFORMATION: BMPRII gene exon2-3 Reverse primer

<400> SEQUENCE: 17
ccaatgtgag accaacatcc t                                               21

<210> SEQ ID NO 18
<211> LENGTH: 21
<212> TYPE: DNA
<213> ORGANISM: Artificial Sequence
<220> FEATURE:
<223> OTHER INFORMATION: BMPRII gene exon5-6 Forward primer

<400> SEQUENCE: 18
ctgctgcagc tcttcttaac t                                               21

<210> SEQ ID NO 19
<211> LENGTH: 21
<212> TYPE: DNA
<213> ORGANISM: Artificial Sequence
<220> FEATURE:
<223> OTHER INFORMATION: BMPRII gene exon5-6 Reverse primer

<400> SEQUENCE: 19
cgctcatcca aggaaccttt a                                               21

<210> SEQ ID NO 20
<211> LENGTH: 23
<212> TYPE: DNA
<213> ORGANISM: Artificial Sequence
<220> FEATURE:
<223> OTHER INFORMATION: BMPRII gene exon1-2 and 5-6 Forward primer -continued

<400> SEQUENCE: 20
ctaactcaca gagattgcct acc                                          23

<210> SEQ ID NO 21
<211> LENGTH: 21
<212> TYPE: DNA
<213> ORGANISM: Artificial Sequence
<220> FEATURE:
<223> OTHER INFORMATION: BMPRII gene exon1-2 and 5-6 Reverse primer

<400> SEQUENCE: 21
cccagctcct ccactttatt t                                            21

<210> SEQ ID NO 22
<211> LENGTH: 408
<212> TYPE: PRT
<213> ORGANISM: Artificial Sequence
<220> FEATURE:
<223> OTHER INFORMATION: rhBMP4 protein

<400> SEQUENCE: 22

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

```
Arg Ala Lys Arg Ser Pro Lys His His Ser Gln Arg Ala Lys Lys
        290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

<210> SEQ ID NO 23
<211> LENGTH: 564
<212> TYPE: DNA
<213> ORGANISM: Artificial Sequence
<220> FEATURE:
<223> OTHER INFORMATION: DHFR

<400> SEQUENCE: 23

```
atggttcgac cattgaactg catcgtcgcc gtgtcccaaa atatgggat tggcaagaac    60
ggagaccta cctggcctcc gctcaggaac gagttcaagt acttccaaag aatgaccaca   120
acctcttcag tggaaggtaa acagaatctg gtgattatgg gtaggaaaac ctggttctcc   180
attcctgaga agaatcgacc tttaaaggac agaattaata tagttctcag tagaaactc   240
aaagaaccac cacgaggagc tcatttctt gccaaaagtt tggatgatgc cttaagactt   300
attgaacaac cggaattggc aagtaaagta gacatggttt ggatagtcgg aggcagttct   360
gtttaccagg aagccatgaa tcaaccaggc cacctcagac tctttgtgac aaggatcatg   420
caggaatttg aaagtgacac gttttctccca gaaattgatt tggggaaata taaacttctc   480
ccagaatacc caggcgtcct ctctgaggtc caggaggaaa aaggcatcaa gtataagttt   540
gaagtctacg agaagaaaga ctaa                                          564
```

<210> SEQ ID NO 24
<211> LENGTH: 35
<212> TYPE: DNA
<213> ORGANISM: Artificial Sequence
<220> FEATURE:
<223> OTHER INFORMATION: BMPRIA KO_22_1

<400> SEQUENCE: 24
agtaacactt taagaaaggc taaagtcact ccatt    35

<210> SEQ ID NO 25
<211> LENGTH: 48
<212> TYPE: DNA
<213> ORGANISM: Artificial Sequence
<220> FEATURE:
<223> OTHER INFORMATION: BMPRIA KO_22_2

<400> SEQUENCE: 25
agtaacactt taagaaaggc aaagttccgg ggctaaagtc actccatt    48

<210> SEQ ID NO 26
<211> LENGTH: 53
<212> TYPE: DNA
<213> ORGANISM: Artificial Sequence
<220> FEATURE:
<223> OTHER INFORMATION: BMPRIA KO_22_3

<400> SEQUENCE: 26
agtaacactt taagaaaggc aaagtatcct tccggggcta aagtcactcc att        53

<210> SEQ ID NO 27
<211> LENGTH: 50
<212> TYPE: DNA
<213> ORGANISM: Artificial Sequence
<220> FEATURE:
<223> OTHER INFORMATION: BMPRIA KO_35_1

<400> SEQUENCE: 27
agtaacactt taagaaaggc aaagtattcc ggggctaaag tcactccatt             50

<210> SEQ ID NO 28
<211> LENGTH: 48
<212> TYPE: DNA
<213> ORGANISM: Artificial Sequence
<220> FEATURE:
<223> OTHER INFORMATION: BMPRIA KO_35_2

<400> SEQUENCE: 28
agtaacactt taagaaaggc aaagtaccgg ggctaaagtc actccatt               48

<210> SEQ ID NO 29
<211> LENGTH: 53
<212> TYPE: DNA
<213> ORGANISM: Artificial Sequence
<220> FEATURE:
<223> OTHER INFORMATION: BMPRIA KO_35_3

<400> SEQUENCE: 29
agtaacactt taagaaaggc aaagtatcct tccggggcta aagtcactcc att        53

<210> SEQ ID NO 30
<211> LENGTH: 54
<212> TYPE: DNA
<213> ORGANISM: Artificial Sequence
<220> FEATURE:
<223> OTHER INFORMATION: BMPRIA KO_35_4

<400> SEQUENCE: 30
agtaacactt taagaaaggc aaagtatcct ttccggggct aaagtcactc catt       54

<210> SEQ ID NO 31
<211> LENGTH: 53
<212> TYPE: DNA
<213> ORGANISM: Artificial Sequence
<220> FEATURE:
<223> OTHER INFORMATION: BMPRIA KO_43

<400> SEQUENCE: 31
agtaacactt taagaaaggc aaagtatcct tccggggcta aagtcactcc att        53

<210> SEQ ID NO 32
<211> LENGTH: 17
<212> TYPE: DNA
<213> ORGANISM: Artificial Sequence
<220> FEATURE:
<223> OTHER INFORMATION: BMPRIA KO_47_1

```
<400> SEQUENCE: 32
agtaaagtca ctccatt                                                        17

<210> SEQ ID NO 33
<211> LENGTH: 50
<212> TYPE: DNA
<213> ORGANISM: Artificial Sequence
<220> FEATURE:
<223> OTHER INFORMATION: BMPRIA KO_47_2

<400> SEQUENCE: 33
agtaacactt taagaaaggc aaagtatacc ggggctaaag tcactccatt                    50

<210> SEQ ID NO 34
<211> LENGTH: 167
<212> TYPE: DNA
<213> ORGANISM: Artificial Sequence
<220> FEATURE:
<223> OTHER INFORMATION: BMPRIA KO_61

<400> SEQUENCE: 34
agtaacactt taagaaaggc aaagtatcct cagaccatcc tggacttcct gaagagcgac         60
ggcttcgcca accgcaactt catgcagctg atccacgacg acagcctgac cttcaaggag        120
gacatccaga aggcccaggt gagcgtcggg gctaaagtca ctccatt                      167

<210> SEQ ID NO 35
<211> LENGTH: 101
<212> TYPE: DNA
<213> ORGANISM: Artificial Sequence
<220> FEATURE:
<223> OTHER INFORMATION: BMPRIA KO_68

<400> SEQUENCE: 35
agtaacactt taagaaaggc aaagtatcct ctggtcttgg aacacttcca aatctcagtg         60
aaaagcgaag ccagtgtttc cggggctaaa gtcactccat t                           101
```